US011786661B2

(12) United States Patent
Koska

(10) Patent No.: US 11,786,661 B2
(45) **Date of Patent: *Oct. 17, 2023**

(54) SINGLE USE DELIVERY DEVICE

(71) Applicant: Koska Family Limited, East Sussex (GB)

(72) Inventor: Marc Andrew Koska, East Sussex (GB)

(73) Assignee: KOSKA FAMILY LIMITED, East Sussex (GB)

( * ) Notice: Subject to any disclaimer, the term of this patent is extended or adjusted under 35 U.S.C. 154(b) by 390 days.

This patent is subject to a terminal disclaimer.

(21) Appl. No.: 17/072,498

(22) Filed: Oct. 16, 2020

(65) Prior Publication Data

US 2021/0030965 A1 Feb. 4, 2021

Related U.S. Application Data

(63) Continuation of application No. 15/741,012, filed as application No. PCT/IB2016/001050 on Jul. 1, 2016, now Pat. No. 10,835,678.

(Continued)

(51) Int. Cl.

*A61M 5/24* (2006.01)
*A61M 5/28* (2006.01)

(Continued)

(52) U.S. Cl.

CPC .......... *A61M 5/2448* (2013.01); *A61M 5/282* (2013.01); *A61M 5/50* (2013.01);

(Continued)

(58) Field of Classification Search

CPC ...... A61M 5/3216; A61M 5/50; A61M 5/282; A61M 5/3202; A61M 5/3205; A61M 2005/3128; A61M 2037/0023

See application file for complete search history.

(56) References Cited

U.S. PATENT DOCUMENTS

| | | | |
|---|---|---|---|
| 2,667,165 | A | 1/1954 | Smith |
| 2,717,598 | A | 9/1955 | Krasno |

(Continued)

FOREIGN PATENT DOCUMENTS

| | | |
|---|---|---|
| AU | 2337470 | 6/1972 |
| EP | 0310227 | 4/1989 |

(Continued)

OTHER PUBLICATIONS

International Search Report for PCT/US18/61696 dated Mar. 7, 2019; 2 pps.

(Continued)

*Primary Examiner* — Nathan R Price
*Assistant Examiner* — Justin L Zamory
(74) *Attorney, Agent, or Firm* — Rowan Tree Law Group, PLLC; Carson C. K. Fincham

(57) ABSTRACT

The invention is a single use delivery device configured to enable reconstitution of a lyophilized agent (e.g., vaccine, drug, medicament, etc.) stored within for subsequent delivery of the reconstituted fluid agent to a patient in a controlled manner and without requiring specialized skill in reconstituting the agent or administering delivery of such agent. The delivery device is prefilled with an individual dose of a lyophilized agent and configured to be filled on-site and in the field with a dose of diluent for reconstitution of the lyophilized agent, while remaining sterile and preventing the potential for contamination during the filling process. The delivery device is further configured to be rendered incapable of reuse followings its intended use of delivering the fluid agent to a patient, thereby preventing reuse of the device and reducing the risk of the spreading blood-borne diseases through reuse.

20 Claims, 12 Drawing Sheets

Related U.S. Application Data

(60) Provisional application No. 62/188,137, filed on Jul. 2, 2015.

(51) Int. Cl.

| | |
|---|---|
| ***A61M 5/50*** | (2006.01) |
| *A61M 5/32* | (2006.01) |
| *A61M 39/24* | (2006.01) |
| *A61M 5/30* | (2006.01) |
| *A61M 5/46* | (2006.01) |
| *A61M 5/31* | (2006.01) |

(52) U.S. Cl.
CPC ............ *A61M 5/30* (2013.01); *A61M 5/3202* (2013.01); *A61M 5/3205* (2013.01); *A61M 5/3216* (2013.01); *A61M 5/46* (2013.01); *A61M 39/24* (2013.01); *A61M 2005/3114* (2013.01); *A61M 2005/3128* (2013.01)

(56) References Cited

U.S. PATENT DOCUMENTS

| | | | | |
|---|---|---|---|---|
| 3,192,925 | A | 7/1965 | Cunningham | |
| 3,640,388 | A | 2/1972 | Ferrari | |
| 4,022,206 | A | 5/1977 | Hilleman | |
| 4,671,763 | A | 6/1987 | Weiler | |
| 4,883,473 | A | 11/1989 | Thomas | |
| 4,955,871 | A | 9/1990 | Thomas | |
| 4,966,581 | A | 10/1990 | Landau | |
| 5,135,514 | A | 8/1992 | Kimber | |
| 5,139,489 | A * | 8/1992 | Hollister | A61M 5/3216 600/576 |
| 5,217,480 | A | 6/1993 | Haber | |
| 5,222,948 | A | 6/1993 | Glenn et al. | |
| 5,261,881 | A | 11/1993 | Riner | |
| 5,509,906 | A | 4/1996 | Poynter | |
| 5,533,505 | A | 7/1996 | Kallstrand | |
| 5,624,407 | A | 4/1997 | Claro | |
| 5,636,640 | A | 6/1997 | Staehlin | |
| D425,617 | S | 5/2000 | Snedden | |
| 6,231,559 | B1 | 5/2001 | Loretti | |
| D447,560 | S | 9/2001 | Hellberg | |
| 6,379,342 | B1 | 4/2002 | Levinson | |
| 6,383,166 | B1 | 5/2002 | Farris | |
| D458,366 | S | 6/2002 | Hellberg | |
| D462,760 | S | 9/2002 | Ahlgrim | |
| 6,663,188 | B2 | 12/2003 | Sumi | |
| 6,860,405 | B1 | 3/2005 | Poynter | |
| 7,028,862 | B2 | 4/2006 | Poynter | |
| 7,100,600 | B2 | 9/2006 | Loeffler | |
| 7,487,894 | B2 | 2/2009 | Zahn | |
| 7,513,397 | B2 | 4/2009 | Zahn | |
| 7,632,253 | B2 | 12/2009 | Ooyauchi | |
| 7,883,660 | B2 | 2/2011 | Matsuda et al. | |
| 7,892,211 | B2 | 2/2011 | McCulloch | |
| 8,133,202 | B2 | 3/2012 | Marsh | |
| 8,434,643 | B2 | 5/2013 | Harris | |
| 8,464,918 | B1 | 6/2013 | Harris | |
| 8,652,096 | B2 | 2/2014 | Alvey | |
| 8,663,188 | B2 | 3/2014 | Genosar | |
| 8,795,226 | B2 | 8/2014 | Kuhn et al. | |
| 9,132,238 | B2 | 9/2015 | Ferreri | |
| 9,242,051 | B2 | 1/2016 | Jugl et al. | |
| 9,265,889 | B2 | 2/2016 | Thornton | |
| D753,292 | S | 4/2016 | Oathes, II | |
| 9,364,393 | B1 | 6/2016 | Grabowski | |
| 9,526,839 | B2 | 12/2016 | Chia | |
| D776,266 | S | 1/2017 | Dombrowski | |
| 9,737,664 | B2 | 8/2017 | Gardner | |
| 9,808,608 | B2 | 11/2017 | Webb | |
| 9,820,913 | B2 | 11/2017 | Genosar | |
| 10,118,000 | B2 | 11/2018 | Schraga | |
| 10,149,939 | B2 | 12/2018 | Giambattista et al. | |
| 10,207,053 | B2 | 2/2019 | Groskoff et al. | |
| 10,278,896 | B2 | 5/2019 | Brandenburger | |
| D859,647 | S | 9/2019 | Chang | |
| 10,512,591 | B2 | 12/2019 | Oshgan et al. | |
| 10,525,212 | B2 | 1/2020 | Thornton | |
| 10,821,053 | B2 | 11/2020 | Rajagopal et al. | |
| 2003/0050602 | A1 | 3/2003 | Pettis et al. | |
| 2003/0186456 | A1 | 10/2003 | Stroup | |
| 2004/0118477 | A1 | 6/2004 | Desmond | |
| 2007/0260188 | A1 | 11/2007 | Kelly et al. | |
| 2008/0083691 | A1 | 4/2008 | Poynter | |
| 2009/0025823 | A1 | 1/2009 | Hansen | |
| 2009/0230077 | A1 | 9/2009 | Poynter | |
| 2011/0224640 | A1 | 9/2011 | Kuhn et al. | |
| 2011/0135720 | A1 | 12/2011 | Marshall | |
| 2012/0083744 | A1 | 4/2012 | Finke et al. | |
| 2012/0179109 | A1 | 7/2012 | Takemoto et al. | |
| 2013/0110053 | A1 | 5/2013 | Yoshino et al. | |
| 2013/0345672 | A1 | 12/2013 | Ferreri | |
| 2013/0345673 | A1 | 12/2013 | Ferreri | |
| 2014/0008366 | A1* | 1/2014 | Genosar | A61M 5/2046 220/265 |
| 2014/0323975 | A1 | 10/2014 | Thornton et al. | |
| 2016/0074586 | A1 | 3/2016 | Mernoe et al. | |
| 2016/0144130 | A1 | 5/2016 | Thornton | |
| 2018/0072480 | A1 | 3/2018 | Genosar | |
| 2018/0235840 | A1 | 8/2018 | Genosar | |
| 2019/0046402 | A1 | 2/2019 | Besbrosses et al. | |
| 2019/0060573 | A1 | 2/2019 | Consolaro et al. | |
| 2019/0224424 | A1 | 7/2019 | Helmer et al. | |
| 2020/0100985 | A1 | 4/2020 | Auerbach | |
| 2020/0129698 | A1 | 4/2020 | Chowdhury | |
| 2020/0164563 | A1 | 5/2020 | Spallek | |

FOREIGN PATENT DOCUMENTS

| | | |
|---|---|---|
| EP | 0388360 | 9/1990 |
| EP | 0903180 | 3/1999 |
| EP | 1726285 | 11/2006 |
| EP | 2665502 | 7/2012 |
| EP | 2554201 | 6/2013 |
| EP | 2554207 | 6/2013 |
| EP | 2571553 | 6/2014 |
| EP | 3173113 | 5/2017 |
| EP | 3518860 | 4/2018 |
| EP | 2919834 | 5/2018 |
| GB | 2490111 | 10/2012 |
| IN | 201741030340 | 1/2019 |
| JP | 2015109883 | 6/2015 |
| KR | 200345715 | 3/2004 |
| KR | 100615527 | 8/2006 |
| WO | WO 1989/007462 | 8/1989 |
| WO | WO 1993/017728 | 9/1993 |
| WO | WO1997010156 | 3/1997 |
| WO | WO1998025660 | 6/1998 |
| WO | WO 2001/043799 | 6/2001 |
| WO | WO2001043799 | 6/2001 |
| WO | WO 2011/008190 | 1/2011 |
| WO | WO2011026050 | 3/2011 |
| WO | WO 2011/075798 | 6/2011 |
| WO | WO2012011115 | 1/2012 |
| WO | WO2012064761 | 5/2012 |
| WO | WO2012099898 | 7/2012 |
| WO | WO2012148043 | 11/2012 |
| WO | WO2013114357 | 8/2013 |
| WO | WO2014035935 | 3/2014 |
| WO | WO2015045740 | 2/2015 |
| WO | WO2015036536 | 3/2015 |
| WO | WO 2015/074087 | 5/2015 |
| WO | WO2017001925 | 1/2017 |
| WO | WO2017125859 | 7/2017 |
| WO | WO2017187262 | 11/2017 |

OTHER PUBLICATIONS

Written Opinion or PCT/US18/61696 dated Mar. 7, 2019; 3 pps.
Office Action for U.S. Appl. No. 15/741,009 dated Oct. 2, 2019; 6 pps.

(56) References Cited

OTHER PUBLICATIONS

Office Action for U.S. Appl. No. 15/741,011 dated Oct. 2, 2019; 8pps.
Notice of Grant for 16774977.9 dated Mar. 12, 2020; 2 pps.
Syrette "https://en.wikipedia.org/wiki/Syrette" download date: Apr. 23, 2020; 2 pps.
International Search Report for PCT/US2019/038302 dated Dec. 19, 2019; 2 pps.
Written Opinion for PCT/US2019/038302 dated Dec. 19, 2019; 4pps.
Written Opinion for WO 2016097872 dated May 6, 2016; 2 pps.
International Search Report for WO 2016097872 dated May 9, 1 pps.
Written Opinion for PCT/IB216/001042 dated Dec. 20, 2016; 6 pps.
Written Opinion for PCT/IB2016/001026 dated Nov. 7, 2016; 5 pps.
International Search Report or PCT/IB2016/001026 dated Nov. 8, 2016; 3 pps.
Written Opinion for PCT/IB2016/001027 dated Nov. 2, 2016; 5 pps.
International Search Report for PCT/IB2016/001027 dated Jan. 5, 2017; 2 pps.
Written Opinion for PCT/IB2016/001033 dated Dec. 7, 2016; 6 pps.
Written Opinion for PCT/IB2016/001050 dated Nov. 14, 2016; 5 pps.
International Search Report for PCT/IB2016/001050 dated Nov. 15, 2016; 2 ops.
Written Opinion for PCT/IIB2016/001034 dated Dec. 9, 2016; 6 pps.
Examination Report for PCT/IB2015/002531 dated May 28, 2020; 5 pps.
International Preliminary Report on Patentability for PCT/US18/61696 dated May 28, 2020; 4pps.
Written Opinion for WO2017/187262 dated Sep. 1, 2017; 7 pps.
International Search Report for WO2017/187262 dated Nov. 2, 2017; 3 pps.
Final Office Action for U.S. Appl. No. 15/741,012 dated Oct. 10, 2019; 7 pps.
Notice of Allowance for U.S. Appl. No. 15/741,012 dated Jul. 10, 2020; 7 pps.

* cited by examiner

SINGLE USE DELIVERY DEVICE

CROSS-REFERENCE TO RELATED APPLICATIONS

This application claims benefit and priority under 35 U.S.C. § 120 to, and is a Continuation of, U.S. patent application Ser. No. 15/741,012 filed on Dec. 29, 2017 and titled "SINGLE USE DELIVERY DEVICE PREFILLED WITH A RECONSTITUTABLE AGENT", which issued as U.S. Pat. No. 10,835,678 on Nov. 17 , 2020, and which itself claims benefit and priority to and is a National Stage application of International Patent Application No. PCT/IB2016/001050 filed on Jul. 1, 2016, which itself claims benefit and priority to U.S. Provisional Patent Application No. 62/188,137 filed on Jul. 2, 2015, the contents of each of which are hereby incorporated by reference herein in their entirety.

FIELD OF THE INVENTION

The present invention generally relates to delivery devices for delivering substances, such as medicaments, and, more particularly, to a single use delivery device configured to enable reconstitution of a lyophilized agent stored within for subsequent delivery of the reconstituted fluid agent to a patient, wherein the device is rendered incapable of reuse following its intended use of delivering the reconstituted fluid agent to a patient.

BACKGROUND

Every year, millions of people become infected and die from a variety of diseases, some of which are treatable or entirely preventable. For example, many diseases may be prevented via immunization programs which include the administration of vaccines. Although vaccination has led to a dramatic decline in the number of cases of several infectious diseases, some of these diseases remain quite common. In many instances, large populations of the world, particularly in developing countries, suffer from the spread of vaccine-preventable diseases due to ineffective immunization programs, either because of poor implementation, lack of affordable vaccines, or inadequate devices for administering vaccines, or combinations thereof.

As part of an ongoing effort to address inadequacies of immunization programs globally, there has been increasing focus on the manner in which vaccines are packaged and provided. For example, in many parts of the world, vaccinations may be supplied in multi-dose containers or vials. A multi-dose vial is a vial of liquid that contains more than one dose of medication and may be used for providing multiple doses for a single individual or for providing a single dose for multiple individuals in a group. In contrast, single-dose format generally includes single-dose vials or prefilled single dose delivery devices.

The multi-dose format may be a more attractive option for various reasons. For example, a multi-dose format may be more cost-effective, as the filling and packaging costs for multi-dose vials are generally cheaper than single-dose vials, and multi-dose vials generally have less cold chain capacity requirements (e.g., less packed volume per dose) when compared to single-dose vials. Furthermore, the distribution of a vaccine within a given population may be improved with the use of multi-dose format, as the multi-dose format has less cold chain requirements and a larger volume of vaccine (e.g. more doses) can be available at a single instance.

Some vaccines (or other medicaments) have a relatively short shelf-life, as they may contain compounds that degrade rapidly and lose their effectiveness. As such, vaccines may require refrigeration and special packaging. Such special treatment, however, adds to operating costs, complicates storage, and offsets the many efficiencies provided by pre-filled single or multi-dose formats. Accordingly, it has become more common for some vaccines (e.g., 20-30% of vaccines used in UNICEF) to be stored in a powdered, or lyophilized form, until a time in which they are to be administered to patients. At a point of use (e.g., in the field), a measured amount of diluent may then be added to a lyophilized vaccine so as to reconstitute the vaccine into a liquid form that is suitable for administration to patients.

Although the multi-dose format may provide numerous advantages as described above, the multi-dose format has drawbacks. For example, the process of reconstituting a lyophilized vaccine in a multi-dose vial (or other multi-dose format) can be cumbersome and may require specialized training or skill. In particular, a certain amount of lyophilized vaccine may be stored within a multi-dose vial and, shortly prior to use, the lyophilized vaccine must be reconstituted with a diluent (e.g., fluid for dissolving the vaccine or otherwise placing the vaccine into liquid form). The reconstitution process generally requires a user (e.g., medical professional, administrator of vaccine, etc.) to first draw up a diluent with a long needle into a transfer syringe, at which point the user must ensure that the syringe includes the correct amount of diluent. Then, the user injects the measured diluent into the multi-dose vial, and further agitates (e.g., shakes) the vial to cause the diluent to evenly mix with the lyophilized vaccine. At this point, the multi-dose vial is ready to dispense multiple doses of vaccine.

In addition to the burdensome reconstitution process, the multi-dose vial must be handled with care so as to protect against cross-contamination, particularly if a multi-dose vial is to be used for more than one patient. If care is not taken by the medical professional administering the vaccine, inadvertent contamination of a multi-dose vial may occur through direct or indirect contact with potentially contaminated surfaces or equipment that could then lead to infections in subsequent patients. For example, a vaccine may be administered via injection with a syringe having a needle. Accordingly, a new, sterile needle and sterile syringe should always be used to access the vaccine in a multi-dose vial. Reuse of needles or syringes to access a vaccine can result in contamination of the vaccine that can be spread to others when the medicine is used again. In many situations, particularly in developing countries, the administration of vaccines occurs outside of a hospital and may be provided by a non-professional. Such non-professionals may not have formal training, or the resources, for the proper preparation and handling of a reconstituted vaccine, and contamination may occur, thereby increasing the risk of infection and spread of blood-borne diseases.

SUMMARY

The present invention provides a single use delivery device that overcomes the drawbacks of current delivery devices and methods. In particular, the single use delivery device of the present invention is configured to enable reconstitution of a lyophilized agent stored within for subsequent delivery of the reconstituted fluid agent to a patient, wherein the device is rendered incapable of reuse following its intended use of delivering the reconstituted fluid agent to a patient. The delivery device is prefilled with an individual dose of a lyophilized agent (e.g., lyophilized vaccine or medicament), which could be in a powder, granular, brick- or cake-like form. The device is configured to be filled on-site and in the field with a dose of diluent for reconstitution of the lyophilized agent, while remaining sterile and preventing the potential for contamination during the filling process. Accordingly, because the device of the present invention is not prefilled with an active fluid agent (but rather an agent in lyophilized state), the delivery device does not require specific shipment or storage conditions associated with agents in liquid form (e.g., certain temperature (e.g., 2 to 8 degrees Celsius) during shipment or storage, non-exposure to sunlight, etc.), thus cutting down on the overall costs.

The delivery device allows for reconstitution of the lyophilized agent in a relatively simple and precise manner, without requiring specialized training. In particular, the delivery device is designed such that a person preparing the agent for delivery at a point of use (e.g., in the field), need only introduce a predefined volume of diluent into a reservoir containing the lyophilized agent to reconstitute the lyophilized agent into liquid form, thereby resulting in a single dose of reconstituted fluid agent that is suitable for administration to a single patient. Accordingly, the single use device of the present invention overcomes the drawbacks associated with dispensing individual doses of a reconstituted fluid agent to a plurality of delivery devices from a single multi-dose vial. In particular, the device of the present invention cuts out the risk of contamination of a single large multi-dose source, as is the case with a multi-dose vial of reconstituted fluid agent.

The delivery device is further configured to allow delivery of the agent to the patient in a relatively simple manner. In particular, the delivery device is designed such that a person administering the agent (e.g., administrator) need only position the device upon the administration site (e.g., shoulder, arm, chest, nose, ear, eye, etc.), and then fully compress the reservoir containing the dose of reconstituted fluid agent, thereby delivering the correct predefined dosage to the patient.

Accordingly, the delivery device of the present invention does not require a trained, skilled healthcare profession for reconstitution or administration of vaccines or drugs. As such, the delivery device may be particularly useful in situations in which vaccines or drugs are being administered in non-healthcare related facilities (e.g., outside of clinics or hospitals) and given to large numbers of individuals over a short period of time by a non-professional. The delivery device further includes numerous safety features for preventing the potential for reuse, thereby reducing the risk of the spreading blood-borne diseases through reuse. For example, the delivery device is configured to be rendered incapable of reuse following its delivery of the agent to a patient.

In one aspect, the present invention provides a single use delivery device including an administration member for administering a reconstituted fluid agent to a patient and a delivery assembly coupled to the administration member and configured to provide a reconstituted fluid agent to the administration member. The delivery assembly includes a base member having an inlet port configured to receive a diluent from a source and an outlet port coupled to the administration member. The base member further includes a channel providing a fluid pathway from the inlet port to the outlet port and a one-way valve positioned within the fluid pathway of the channel. The one-way valve is configured to limit fluid flow of the diluent to an antegrade direction from the inlet port toward the outlet port.

The delivery assembly further includes a top member coupled to the base member. The top member includes a compressible reservoir member in fluid communication with the fluid pathway of the channel. The reservoir member has a reconstitutable agent stored within an interior volume. The reconstitutable agent may include, but is not limited to, a lyophilized agent, a powdered agent, a granular agent, an agent embedded in a reconstitutable material, and combinations thereof. In some embodiments, the agent is a vaccine. The reservoir member is configured to receive a diluent passing through the one-way valve to enable mixing of the diluent with the agent to thereby reconstitute the agent. The compressible reservoir member is further configured to expel the reconstituted fluid agent into the fluid pathway and through the outlet port into the administration member in response to a compression force applied thereto.

Accordingly, upon receiving a diluent from a source via the inlet port, the one-way valve is configured to only permit unidirectional flow of the diluent from the inlet port through the valve and towards the outlet port via the fluid pathway of the channel. Thus, when filling the delivery device with a diluent from a source, for example, a person need only couple a source (e.g., syringe) to the inlet port and then fill the reservoir with the diluent by applying pressure to a plunger of the syringe. Due to the one-way valve, the diluent is only permitted to flow within the reservoir and prevented from flowing in a retrograde fashion out of the reservoir. Furthermore, the interior volume of the reservoir may be within a range considered to be a dose. Accordingly, rather than requiring a person to closely monitor the exact amount of diluent provided to the delivery device, they need only provide the diluent to the delivery device until the interior volume of the reservoir is completely filled (the interior volume is limited to the dosage amount for any given fluid agent).

In some embodiments, the device may be prefilled with both the reconstitutable agent and diluent in separate reservoirs, which are separated from one another via the one-way valve. Accordingly, upon compression of the reservoir containing the diluent, the diluent may be expelled into the fluid pathway and through the one-way valve and into the reservoir containing the reconstitutable agent to enable mixing of the diluent with the agent to thereby reconstitute the agent. Then, a user need only compress the reservoir containing the reconstituted fluid agent so as to expel the reconstituted fluid agent into the fluid pathway and through the outlet port into the administration member for delivery to a patient. This particular embodiment may be advantageous in instances where a single source of diluent is either unavailable or inefficient from a cost or storage standpoint (e.g., military application).

In some embodiments, the delivery device includes safety features for preventing the potential for reuse of the device. For example, in some embodiments, the top member includes an inelastic material, such that, upon collapse of the reservoir member in response to substantial compression applied thereto, the reservoir member is prevented from being reformed and the interior volume is prevented from expanding. Thus, the reservoir member is rendered incapable of reuse following its delivery of the reconstituted fluid agent to a patient. In some embodiments, the base member further comprises a protector member adjacent to the outlet port and configured to move between a closed position, in which at least a tip of the administrator member is shielded, and an open position, in which the tip of the administration member is exposed. Additionally, or alternatively, the top member may include a valve cover configured to substantially enclose the one-way valve, wherein, upon substantial compression applied to the valve cover, the valve cover is configured to substantially collapse upon the one-way valve and render the one-way valve inoperable, thereby blocking fluid flow from the inlet port to the reservoir member.

In some embodiments, the administration member may include a needle for at least one of subcutaneous, intramuscular, intradermal, and intravenous injection of the reconstituted fluid agent into the patient. In other embodiments, the administration member may include a nozzle configured to control administration of the reconstituted fluid agent to the patient. The nozzle may include a spray nozzle, for example, configured to facilitate dispersion of the reconstituted fluid agent into a spray. Accordingly, a delivery device fitted with a spray nozzle may be particularly useful in the administration of a fluid agent into the nasal passage, for example, or other parts of the body that benefit from a spray application (e.g., ear canal, other orifices). In other embodiments, the nozzle may be configured to facilitate formation of droplets of the fluid agent. Thus, a delivery device including a droplet nozzle may be useful in the administration of a fluid agent by way of droplets, such as administration to the eyes, topical administration, and the like.

In some embodiments, a seal member may cover the inlet port of the base member so as to prevent any contaminants from entering the inlet port and potentially contaminating the delivery device prior to filing the delivery device with the fluid agent. For example, a single use seal member composed of a relatively thin sheet of material (e.g., metal foil, plastic, etc.) may be hermetically sealed to the opening of the inlet port, thereby preventing contaminants (e.g., gases, fluids, dirt, debris, etc.) from entering the delivery device. The seal member is configured to rupture upon coupling of a filler syringe to the inlet port, thereby allowing a fluid to enter into the delivery device via the inlet port. Accordingly, the seal member provides a measure of security to ensure that the delivery device remains sterile until it is to be used. The seal member is generally applied to the delivery device during manufacture and/or assembly of the device. A plurality of empty delivery devices may then be shipped and stored at a desired location and will remain sterile, due, in part, to the seal member, thereby improving the process of storing such devices and the speed of assembly and use of such devices. This also may remove the requirement for individual blister packaging sleeves and allow for bulk packing. Bulk packing is a very big advantage in the market, reducing the individual unit production costs, handling, shipping and storage.

The delivery device may be configured to prevent unintentional needle sticks, or inadvertent contact with the administration member, thus reducing the potential for spreading blood-borne diseases. For example, in some embodiments, the base member further includes a protector member extending from distal end adjacent to the outlet port. The protector member is configured to move between a closed position, in which a tip of the administration member (e.g., needle, nozzle, etc.) is shielded, and an open position, in which the tip of the administration member exposed. Accordingly, needle protector member may be in a closed position while the delivery device is being shipped, stored, and handled (e.g., during filling of the delivery device). An administrator need only move the protector member to an open position to expose the administration member for delivering the fluid agent to a target site on a patient. Upon delivering the fluid agent, the administrator may then move the protector member to a closed position and discard the delivery device.

The base member and top member may be formed of medical grade materials. In some embodiments, the base member and top member may be formed from a thermoplastic polymer, for example. An advantage of the construction of the delivery device is that the base and top members may be produced separately from one another, wherein the base member may have a consistent production size and shape, while production of the top member may vary depending on the dosage amount. For example, certain vaccines require specific dosage amounts. Accordingly, a first production of top members can be produced so as to have a reservoir having an interior volume corresponding to a dosage amount recommended for a first vaccine (e.g., poliovirus vaccine) and a second production of top members can be produced so as to have a reservoir having an interior volume corresponding to dosage amount recommended for a second vaccine (e.g., Hepatitis). Accordingly, different dosage amounts can be easily produced (producing different top members) while still using a universal production of base members. The top member is then sealed to a base member to provide an assembled delivery device.

DETAILED DESCRIPTION

Figure 1:
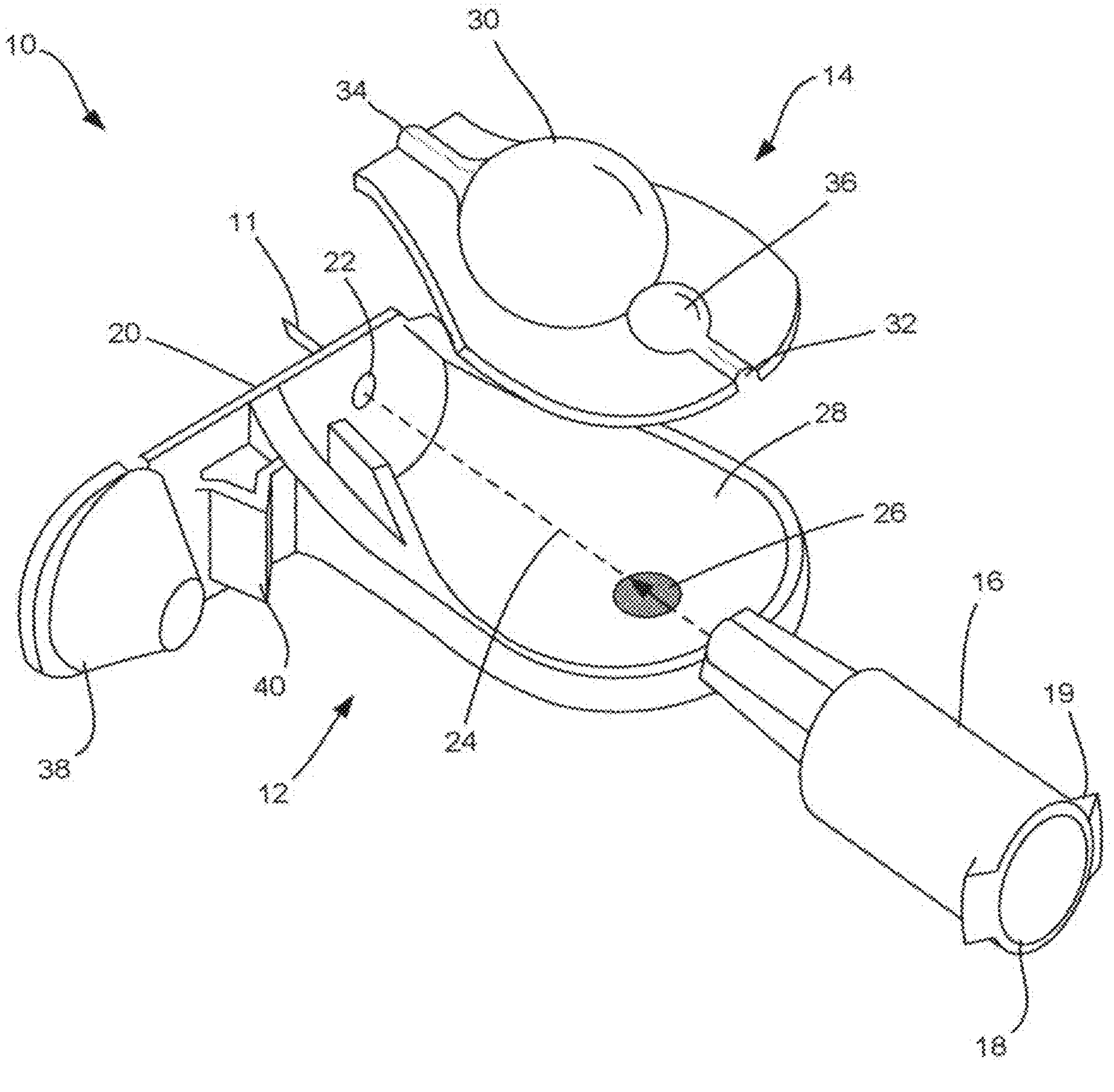
FIG. 1 is a top perspective exploded view of a single use delivery device consistent with the present disclosure.

The present invention provides a single use delivery device of the present invention is configured to enable reconstitution of a lyophilized agent (e.g., vaccine, drug, medicament, etc.) stored within for subsequent delivery of the reconstituted fluid agent to a patient in a controlled manner and without requiring specialized skill in reconstituting the agent or administering delivery of such agent. The delivery device is prefilled with an individual dose of a lyophilized agent (e.g., lyophilized vaccine or medicament), which could be in a powder, granular, brick- or cake-like form. The device is configured to be filled on-site and in the field with a dose of diluent for reconstitution of the lyophilized agent, while remaining sterile and preventing the potential for contamination during the filling process. Accordingly, because the device of the present invention is not prefilled with an active fluid agent (but rather an agent in lyophilized state), the delivery device does not require specific shipment or storage conditions associated with agents in liquid form (e.g., certain temperature (e.g., 2 to 8 degrees Celsius) during shipment or storage, non-exposure to sunlight, etc.), thus cutting down on the overall costs.

By way of overview, the present invention provides a single use delivery device including an administration member for administering a reconstituted fluid agent to a patient and a delivery assembly coupled to the administration member and configured to provide a reconstituted fluid agent to the administration member. The delivery assembly includes a base member having an inlet port configured to receive a diluent from a source and an outlet port coupled to the administration member. The base member further includes a channel providing a fluid pathway from the inlet port to the outlet port and a one-way valve positioned within the fluid pathway of the channel. The one-way valve is configured to limit fluid flow of the diluent to an antegrade direction from the inlet port toward the outlet port.

The delivery assembly further includes a top member coupled to the base member. The top member includes a compressible reservoir member in fluid communication with the fluid pathway of the channel. The reservoir member has a reconstitutable agent stored within an interior volume. The reconstitutable agent may include, but is not limited to, a lyophilized agent, a powdered agent, a granular agent, an agent embedded in a reconstitutable material, and combinations thereof. In some embodiments, the agent is a vaccine. The reservoir member is configured to receive a diluent passing through the one-way valve to enable mixing of the diluent with the agent to thereby reconstitute the agent. The compressible reservoir member is further configured to expel the reconstituted fluid agent into the fluid pathway and through the outlet port into the administration member in response to a compression force applied thereto.

The delivery device allows for reconstitution of the lyophilized agent in a relatively simple and precise manner, without requiring specialized training. In particular, the delivery device is designed such that a person preparing the agent for delivery at a point of use (e.g., in the field), need only introduce a predefined volume of diluent into a reservoir containing the lyophilized agent to reconstitute the lyophilized agent into liquid form, thereby resulting in a single dose of reconstituted fluid agent that is suitable for administration to a single patient. Accordingly, the single use device of the present invention overcomes the drawbacks associated with dispensing individual doses of a reconstituted fluid agent to a plurality of delivery devices from a single multi-dose vial. In particular, the device of the present invention cuts out the risk of contamination of a single large multi-dose source, as is the case with a multi-dose vial of reconstituted fluid agent.

In some embodiments, the device may be prefilled with both the reconstitutable agent and diluent in separate reservoirs, which are separated from one another via the one-way valve. Accordingly, upon compression of the reservoir containing the diluent, the diluent may be expelled into the fluid pathway and through the one-way valve and into the reservoir containing the reconstitutable agent to enable mixing of the diluent with the agent to thereby reconstitute the agent. Then, a user need only compress the reservoir containing the reconstituted fluid agent so as to expel the reconstituted fluid agent into the fluid pathway and through the outlet port into the administration member for delivery to a patient. This particular embodiment may be advantageous in instances where a single source of diluent is either unavailable or inefficient from a cost or storage standpoint (e.g., military application).

The delivery device is further configured to allow delivery of the agent to the patient in a relatively simple manner. In particular, the delivery device is designed such that a person administering the agent (e.g., administrator) need only position the device upon the administration site (e.g., shoulder, arm, chest, nose, ear, eye, etc.), and then fully compress the reservoir containing the dose of reconstituted fluid agent, thereby delivering the correct predefined dosage to the patient. In particular, the delivery device is designed such that a person administering the reconstituted agent (e.g., administrator) need only position the device upon the administration site (e.g., shoulder, arm, chest, nose, ear, eye, etc.), and then fully compress a reservoir containing the dose of reconstituted agent, thereby delivering the correct predefined dosage to the patient. Accordingly, the delivery device of the present invention does not require a trained, skilled healthcare profession for administration of vaccines or drugs. As such, the delivery device may be particularly useful in situations in which vaccines or drugs are being administered in non-healthcare related facilities (e.g., outside of clinics or hospitals) and given to large numbers of individuals over a short period of time by a non-professional. The delivery device further includes numerous safety features for preventing the potential for reuse, thereby reducing the risk of the spreading blood-borne diseases through reuse. For example, the delivery device is configured to be rendered incapable of reuse following its delivery of the reconstituted agent to a patient.

Figure 2:
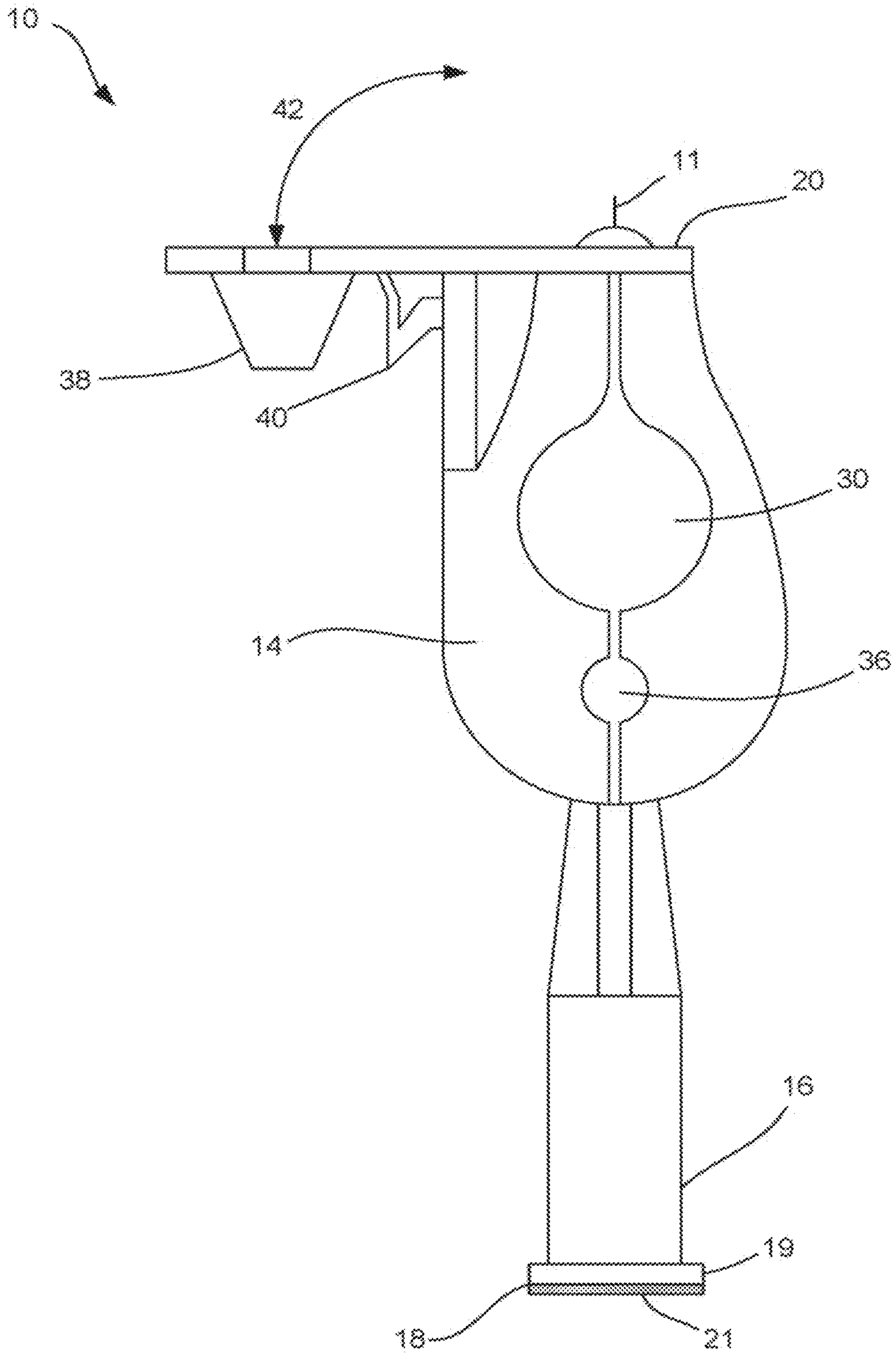
FIG. 2 is a top elevation view of the single use delivery device of FIG. 1 illustrating the base and top members in an assembled state.
Figure 3:
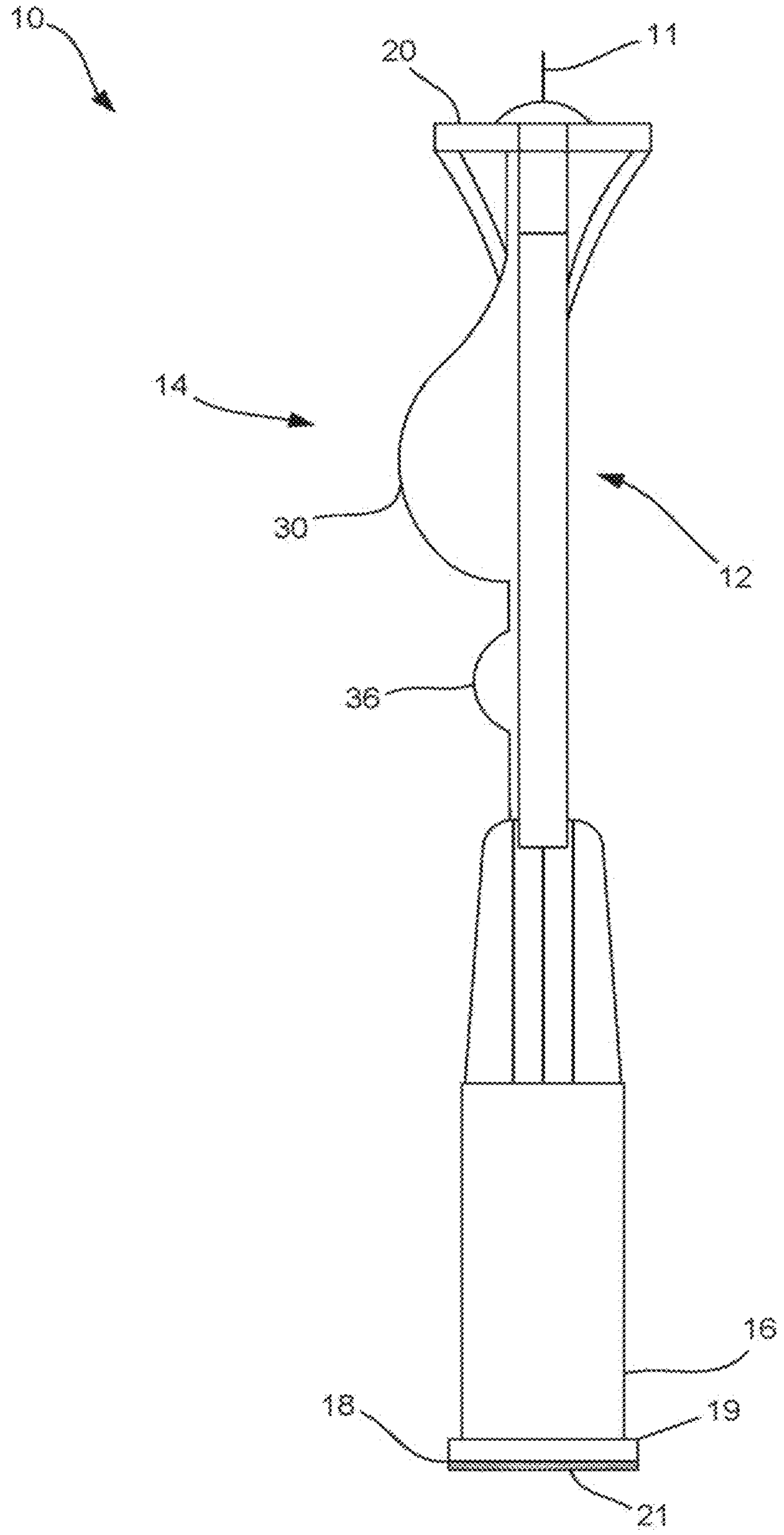
FIG. 3 is side view of the single use delivery device of FIG. 1 illustrating the base and top members in an assembled state.

FIG. 1 is a top perspective exploded view of a single use delivery device 10 consistent with the present disclosure. FIGS. 2 and 3 are top and side elevation views of the single use delivery device 10 in an assembled state. As shown, the single use delivery device 10 may include a needle 11 having a tip configured for penetrating a target site and injecting a fluid agent into the target site. As will be described in greater detail herein, the needle may include a micro-needle configured to penetrate a patient's skin down to a depth of the dermis and deliver a dosage of fluid agent thereto. In other embodiments, however, the needle 11 may be sized for other injection types (e.g., intravenous, subcutaneous, intradermal, etc.). In some embodiments, the single use delivery device 10 of the present disclosure is not limited solely to the administration of a fluid agent via injection, and thus may be fitted with other means of delivering a fluid agent (e.g., nozzle tip, spray tip, droplet tip, etc.) in lieu of a needle.

The device 10 further includes a base member 12 and a top member 14 coupled thereto, wherein the combined base and top members 12, 14 are configured to provide the fluid agent into the needle for subsequent injection. As generally understood, the fluid agent may include any type of agent to be injected into a patient (e.g., mammal, either human or non-human) and capable of producing an effect. Accordingly, the agent may include, but is not limited to, a vaccine, a drug, a therapeutic agent, a medicament, or the like. Furthermore, as will be described in greater detail herein, the agent is initially stored within a portion of the device (e.g., reservoir member) in a lyophilized state in an individual dose. As such, the agent may initially be in a powder, granular, brick- or cake-like form until a diluent is added, at which point the diluent mixes with the lyophilized agent to form a reconstituted fluid agent to be delivered to a patient.

The base member 12 includes a proximal end 16 having an inlet port 18 configured to receive fluid (e.g., a diluent) from a source and a distal end 20 having an outlet port 22 coupled to the needle 11 and configured to provide a reconstituted fluid agent thereto. As described in greater detail herein, the source of the diluent may include a filling syringe, for example, configured to be releasably coupled to the inlet port 18 of the base member 16. As shown, the inlet port 18 may include a Luer-type connection 19, such as a Luer-Lok fitting, configured to releasably engage a corresponding Luer-type connection on a hub of the syringe, thereby providing a fluid connection between the syringe and the inlet port 18 of the base member 12. It should be noted that the inlet port 18 need not be limited to an ISO standard (e.g. ISO 594) luer fitting. In other embodiments, the inlet port 18 may include non-standard connection fittings to be coupled with non-standard connection fitting of a source or adapter, for example. Accordingly, by providing a specialty connection fitting, only approved sources (e.g., multi-dose dispensing devices) can be used with the delivery devices of the present disclosure, thereby adding one more layer of security.

As shown, a seal member 21 may cover the inlet port 18 so as to prevent any contaminants from entering the inlet port 18 and potentially contaminating the delivery device 10 prior to filing the delivery device 10 with the diluent. For example, a single use seal member 21 may be composed of a relatively thin sheet of material (e.g., metal foil, plastic, etc.) may be hermetically sealed to the opening of the inlet port 18, thereby preventing contaminants (e.g., gases, fluids, dirt, debris, etc.) from entering the delivery device 10. The seal member 21 may be coupled to the inlet port 18 by any known sealing techniques (e.g., heat, vibration, or adhesive process). The seal member 21 is configured to be durable in the sense that it provides a sufficient seal with the inlet port 18 and prevent contaminants from entering into the device 10 via the inlet port 18 while also being configured to be pliable and rupture upon coupling of the inlet port 18 to a source (e.g., hub of filler syringe), thereby allowing a fluid to enter into the delivery device 10 via the inlet port 18. Accordingly, the seal member 21 provides a measure of security to ensure that the delivery device 10 remains sterile until it is to be used.

The base member 12 may further include a channel 24 formed within a portion thereof and providing a fluid pathway from the inlet port 18 to the outlet port 22. Upon receipt of diluent from a source, via the inlet port 18, the diluent may flow within the pathway provided by the channel 24. The base member 12 further includes a one-way valve 26 positioned within the fluid pathway of the channel 24. The one-way valve 26 is configured to permit antegrade flow of fluid from the inlet port 18 to the outlet port 22, while preventing retrograde flow (e.g., backflow) of fluid from the outlet port 22 through the valve 26 and through the inlet port 18. For example, the one-way valve 26 may include an open inlet end and an adjustable outlet end configured to move between a normally closed position and an open position. The one-way valve 26 is positioned such that the open inlet end is configured to receive fluid from the inlet port 18, and, upon sufficient application of fluid pressure in a direction away from the inlet port 18 and towards the outlet port 22 (e.g., depressing plunger of filling syringe to fill device 10 with diluent) the outlet end of the valve 26 moves from the normally closed position to an open position to allow fluid to flow therethrough in a direction towards the outlet port 22, as indicated by the directional arrow. When in a closed position, the outlet provides a substantially leak-proof and/or airtight seal so as to prevent any fluid from entering the valve 26 from the outlet end.

Furthermore, the valve 26 is configured such that any application of fluid pressure in a direction away from the outlet port 22 and towards the outlet end of the valve 26, the outlet end remains closed, thereby preventing any fluid from flowing through the valve 26 in a retrograde direction from the outlet port 22 towards the inlet port 18. As generally understood, the one-way valve 26 may include any type of valve configured to permit fluid to flow only in a single direction. The one-way valve 26 may include any type of valve having medical grade material and configured to be used with the flow of fluids. For example, the one-way valve 26 may include a Reed valve or a Heimlich valve.

The top member 14 may be formed separately from the base member 12, which provides advantages, as previously described herein. Accordingly, the top member 14 may be coupled to a portion of the base member 12 along a mounting section 28. For example, the mounting section 28 generally includes a large portion of the base member 12 and includes at least a portion of the channel 24 and the one-way valve 26, such that, upon coupling the top member 14 to the mounting section 28 of the base member 12, the top member substantially encloses the channel 24 and the one-way valve 26.

The top member 14 includes a compressible reservoir member 30 and a compressible valve cover 26, such that, upon coupling the top member 14 to the base member 12, the reservoir member 30 is in fluid communication with the fluid pathway of the channel 24 and the valve cover 36 substantially encloses the one-way valve 26. The top member 14 may further include an inlet 32 and an outlet 34 and a fluid pathway extending there between and in fluid communication with the reservoir member 30 and valve cover 36. Accordingly, once coupled to the base member 12, the inlet 34 and outlet 34 and the pathway extending there between may substantially correspond to the fluid pathway of the channel 24, thereby cooperating with one another to form a combined single channel pathway from the inlet port 18 to the outlet port 22.

The top member 14 may be coupled to the base member 12 by any known means so as to create a hermetic seal. For example, the base and top members 12, 14 may be sealed with one another via any known adhesives, cements, ultrasonic welding, or thermoplastic bonding techniques. The base and top members 12, 14 are composed of a medical grade material. In some embodiments, the base member 12, the top member 14, or both, may be composed of a thermoplastic polymer, including, but not limited to, polypropylene, polyethylene, polybenzimidazole, acrylonitrile butadiene styrene (ABS) polystyrene, polyvinyl chloride, PVC, or the like.

The reservoir member 30 includes an interior volume configured to receive and store an individual dose of a reconstitutable agent (e.g., lyophilized agent) and further receive an amount of diluent passing through the one-way valve 26 to mix with the reconstitutable agent to form a single dose of reconstituted fluid agent. Upon applying a compression force to the reservoir member 30, the reconstituted fluid agent is expelled into the fluid pathway of the channel 24 and through the outlet port 22 into the needle 11. Accordingly, the method of delivering the fluid agent into a patient is a relatively simple and straightforward process which simply requires an administrator to apply sufficient pressure to the filled reservoir member 30 so as to deform the reservoir, resulting in expulsion of the stored fluid agent from the interior volume. Due to the one-way valve 26, the reconstituted fluid agent is force to flow in a direction towards the outlet port 22 and out of the needle 11.

The base member 12 further includes a needle protector member 38 extending from the distal end 20 and adjacent to the outlet port 22. The needle protector member 38 may be coupled to the distal end 20 by way of any known means. In the illustrated embodiment, the needle protector member 38 is coupled to the distal end 20 by way of a living hinge 40, for example. Accordingly, the needle protector member 38 is configured to move between a closed position and an open position, as indicated by arrow 42. When in a closed position, the needle protector member 38 is configured to substantially enclose the penetrating tip of the needle 11, thereby shielding one from inadvertent needle sticks. When in an open position, as shown, the penetrating tip of the needle 11 is exposed and ready for intradermal injection on a target site of a patient. Accordingly, the needle protector member 38 may be in a closed position while the delivery device 10 is being shipped, stored, and handled (e.g., during filling of the delivery device 10). An administrator need only move the needle protector member 38 to an open position to expose the needle 11 for delivering the reconstituted fluid agent to a target site on a patient. Upon delivering the fluid agent, the administrator may then move the needle protector member 38 to a closed position and discard the delivery device 10, so as to prevent unintentional needle sticks.

Figure 4:
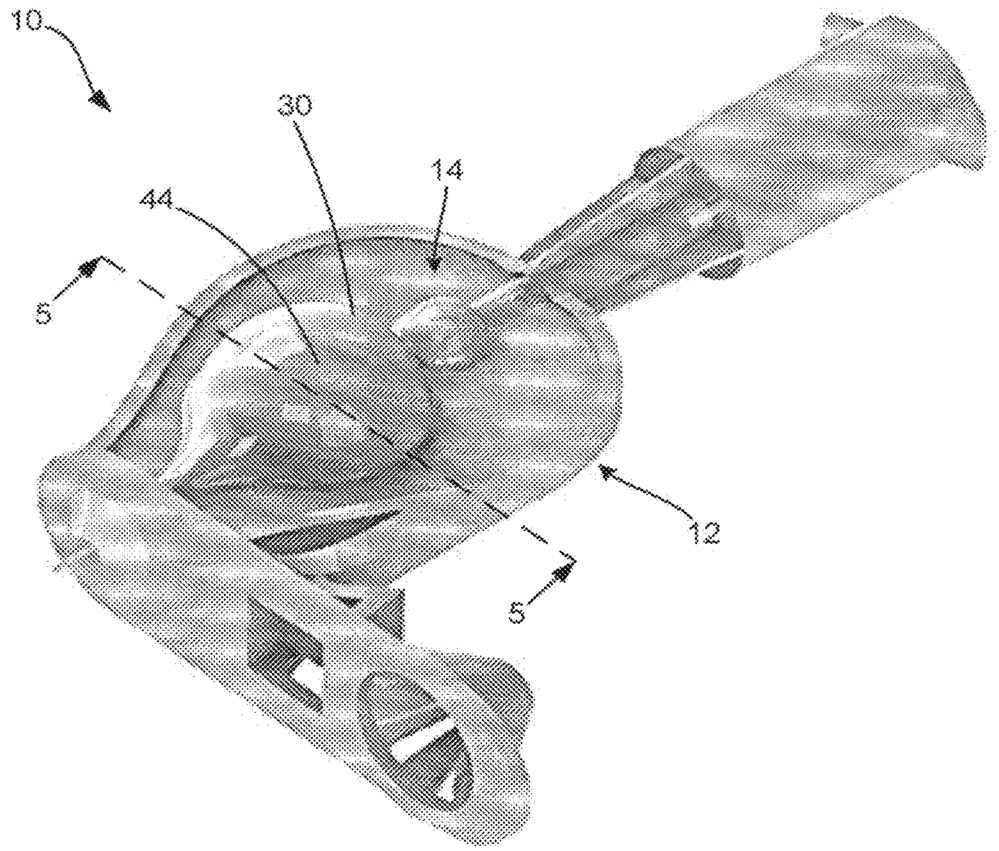
FIG. 4 is a perspective view of a single use delivery device consistent with the present disclosure including a reconstitutable agent stored within an interior volume of the reservoir member.

FIG. 4 is a perspective view of a single use delivery device 10 including a reconstitutable agent 44 stored within an interior volume of the reservoir member 30. As previously described, the device 10 may be prefilled with an individual dose of a lyophilized agent (e.g., lyophilized drug, vaccine, medicament, therapeutic, and the like). As generally understood, lyophilization refers to the process of freeze-drying agents so as to stabilize compounds so they can be reconstituted just prior to administration. This process can protect biological activity, extend shelf life, and even increase dosing precision. As shown, an individual dose of a reconstitutable agent 44 may be provided within the reservoir member 30. In some embodiments, during assembly of the device 10, it is possible to place the reconstitutable agent within the reservoir member 30 so that it is sealed within when the base and top members 12, 14 are sealed to one another. In other embodiments, the reconstitutable agent 44 may be initially dissolved in a liquid that is provided within the reservoir member 30 during manufacture, at which point, the dissolved agent in liquid form may be frozen in within the device 10 at a low temperature (e.g., minus 60° C.). The water or diluent may then be extracted via vacuum, resulting in a porous, dry "lyo cake", at which point, a final drying step may be performed to remove residual unfrozen water molecules, resulting in a final reconstitutable form.

Figure 5:
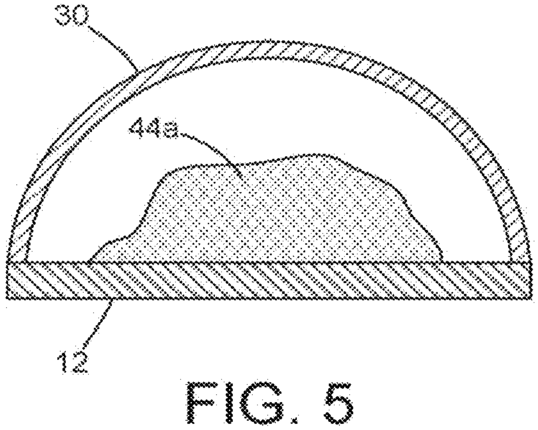
FIG. 5 is a sectional view of the delivery device of FIG. 4 taken along lines 5-5 illustrating the reconstitutable agent in powder or granular form.
Figure 6:
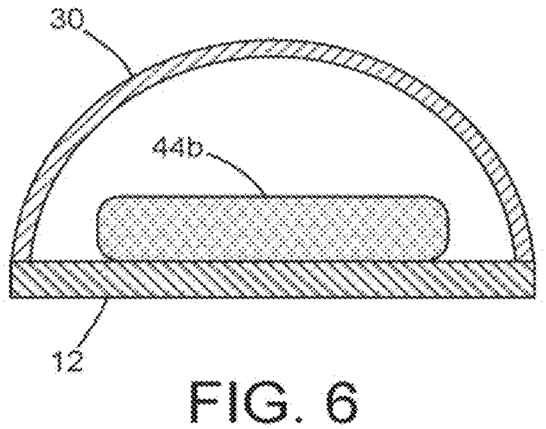
FIG. 6 is a sectional view of the delivery device of FIG. 4 taken along lines 5-5 illustrating the reconstitutable agent in a brick- or cake-like lyophilized form.
Figure 7:
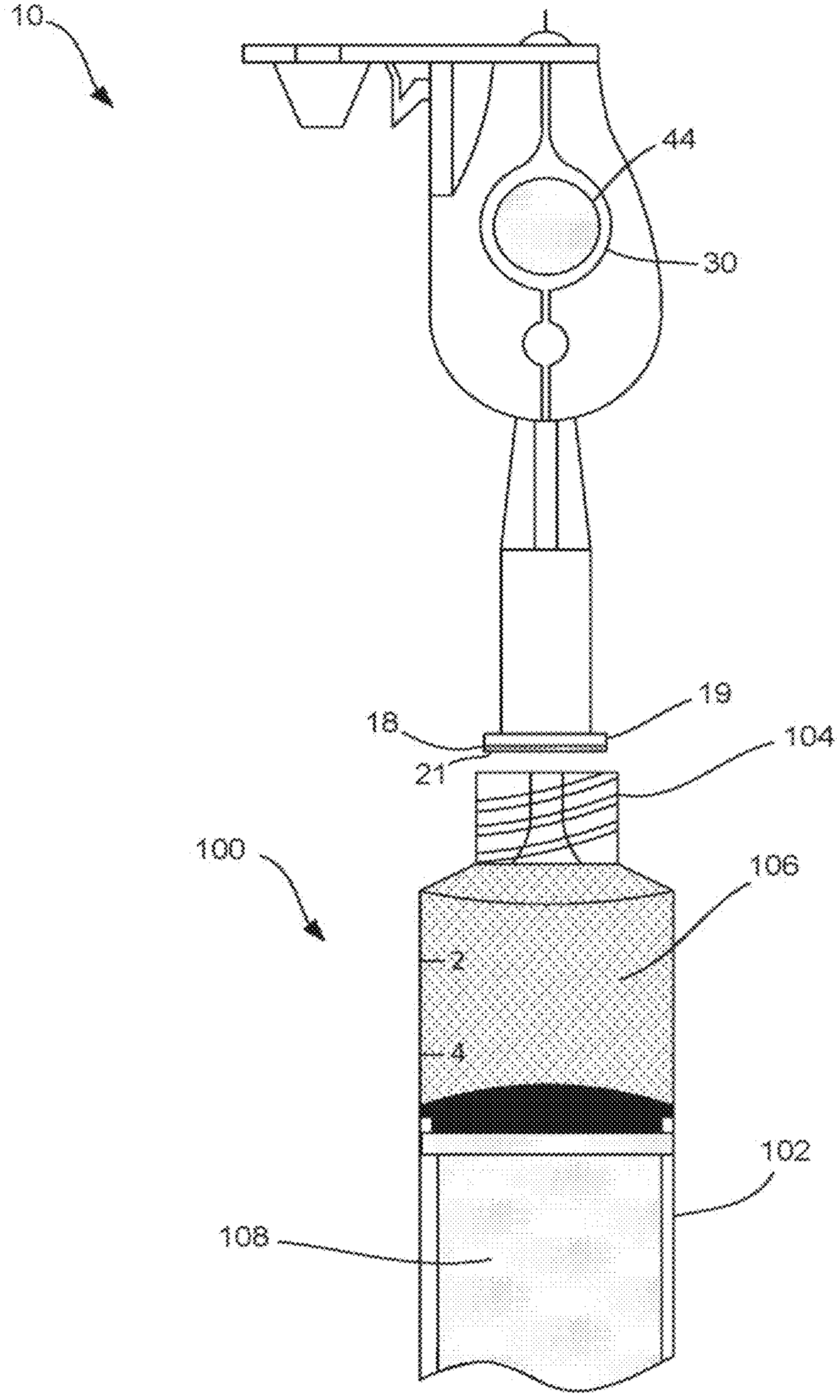
FIGS. 7 and 8 are top elevation views of the single use delivery device of FIG. 4 and a source of diluent illustrating coupling of the single use delivery device to the source and subsequent dispensing of the diluent into the device to mix with the reconstitutable agent.

The reconstitutable agent 44 may be in various dry forms. For example, as shown in FIG. 5, the reconstitutable agent **44*a* may be in powder or granular form. Alternatively, the reconstitutable agent 44*b* may be in a brick- or cake-like form, as shown in FIG. 6. Yet still, in other embodiments, the agent may be embedded in a reconstitutable material, such as a substrate (e.g., non-toxic paper-like material) having the agent embedded, or otherwise infused, within the substrate. For example, the agent may be included within a soluble substrate, such as a paper disc, as shown in FIGS. 6 and 7**. The term "soluble" may generally refer to the quality of being dissolvable, particularly when exposed to direct contact with a liquid or when placed in an environment with a relatively high humidity. Although suggested as a "paper disc", the substrate may take on various forms and need not be limited to a paper material or a disc shape. However, in some embodiments, the substrate may generally be composed of soluble fibers in which the agent has been lyophilized. In the present context, the soluble substrate is generally dissolvable upon contact with the diluent, such that an agent embedded within the substrate is reconstituted and results in a fluid agent to be delivered to the paper. By providing the agent in a soluble substrate, the reconstitutable agent may be easier to handle during manufacturing and assembly, as opposed to some drawbacks of handling a powder, which may present difficulties due to dust and flaking.

The reconstitutable agent 44 may be pre-measured such that the reservoir member 30 is prefilled with an individual dose and, when the device 10 reaches the field, the operator need only fill the reservoir member 30 with a dose of diluent (e.g., water, saline, or other reagent compatible with agent), upon which the agent 44 is reconstituted back into a liquid dose for imminent delivery to a patient through injection, drops or spray, as examples.

The delivery device 10 allows for reconstitution of the agent 44 in a relatively simple and precise manner, without requiring specialized training. In particular, the delivery device 10 is designed such that a person preparing the agent for delivery at a point of use (e.g., in the field), need only introduce a predefined volume of diluent into the reservoir member 30 containing the lyophilized agent 44 to reconstitute the lyophilized agent 44 into liquid form, thereby resulting in a single dose of reconstituted fluid agent that is suitable for administration to a single patient.

Figure 8:
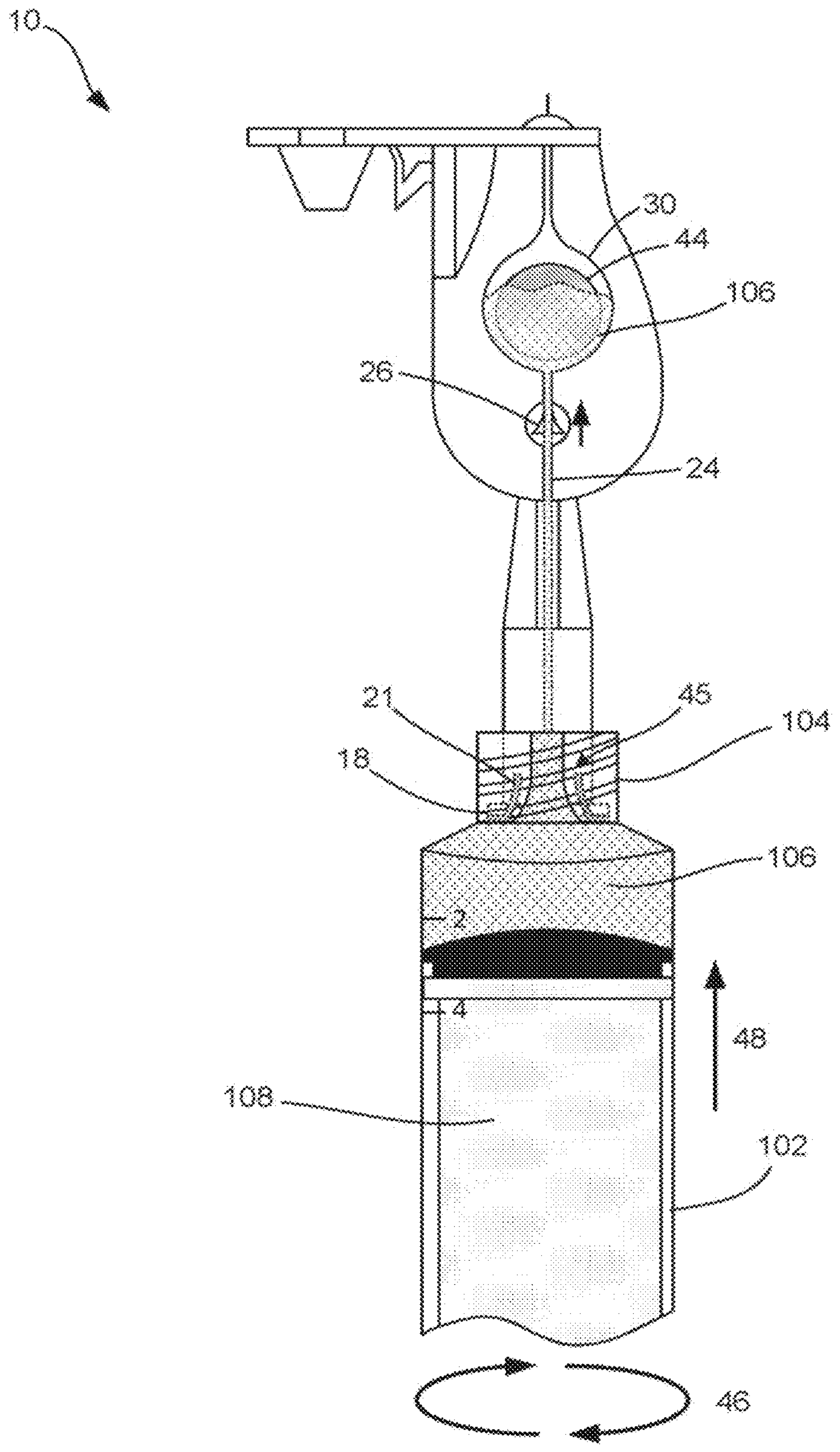

For example, FIGS. 7 and 8 illustrate coupling of the single use delivery device 10 to a multi-dose source for dispensing a diluent into the delivery device 10. In the illustrated embodiment, the source may include a filler syringe 100, for example. The filler syringe 100 may be embodied as a conventional syringe. Accordingly, the filler syringe 100 includes a barrel 102 having a distal hub 104 configured to be releasably coupled to the inlet port 18 of the base member 12 of the delivery device 10. For example, the inlet port 18 may include a Luer-type connection 19, such as a Luer-Lok fitting, configured to releasably engage a corresponding Luer-type connection on the hub 104 of the syringe 100, thereby providing a fluid connection between the interior volume of the barrel 102 of the syringe 100 and the inlet port 18 and subsequent fluid pathway formed by the channel 24 of the base member 12.

Figure 9:
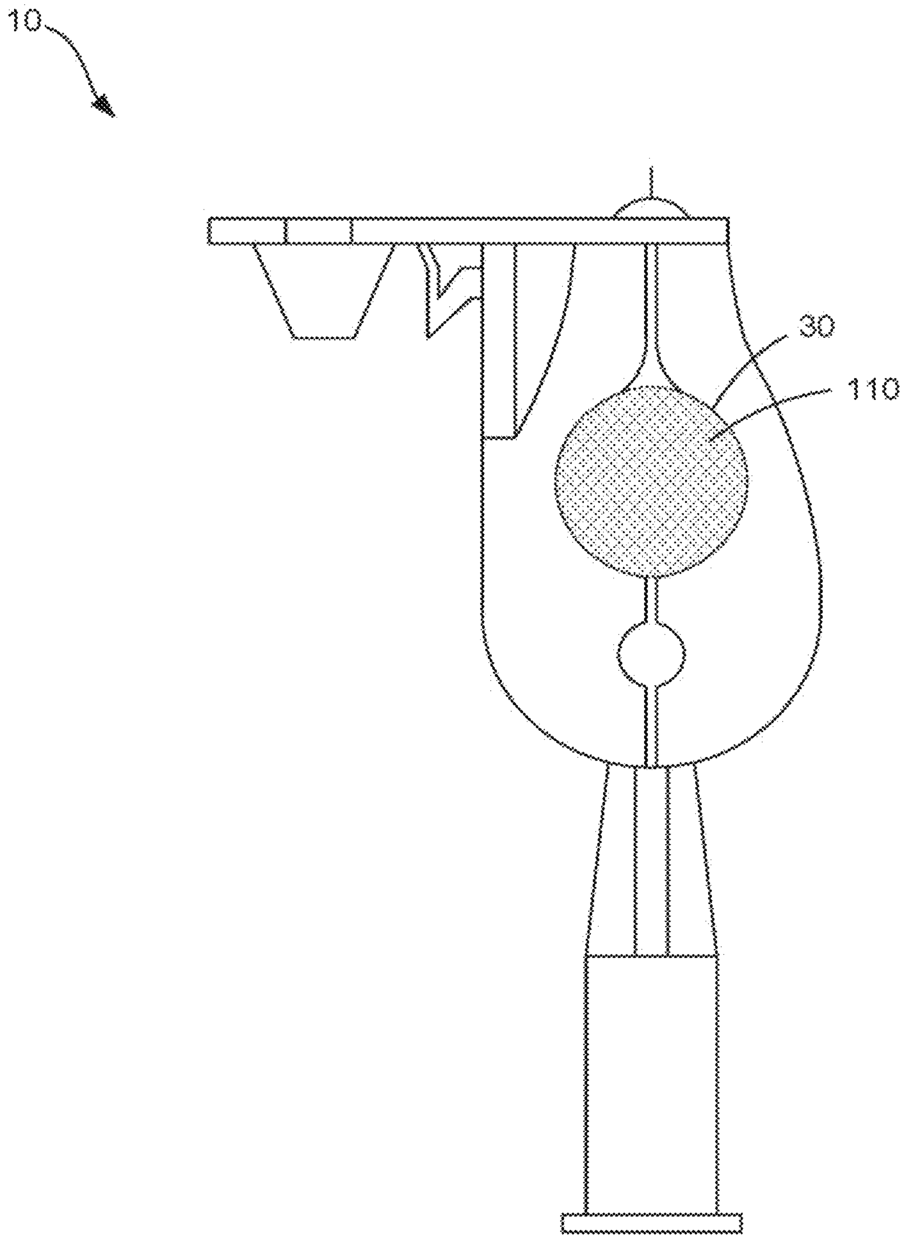
FIG. 9 is a top elevation view of the delivery device of FIG. 4 illustrating the mixing of the reconstitutable agent and diluent to form a reconstituted fluid agent in a form that is acceptable for delivery to a patient.

In order to fill the delivery device 10, specifically the reservoir member 30, with a diluent 106 contained with the syringe 100, a person need only couple the hub 104 with the inlet port 18. As shown in FIG. 7, the seal member 21 is intact and covering the inlet port 18 so as to prevent any contaminants from entering the inlet port 18 and potentially contaminating the delivery device 10 prior to filing the delivery device 10 with the diluent 106. Upon inserting the hub 104 into engagement with the inlet port 18, the hub 104 is configured to pierce the seal member 21, upon which the seal member 21 ruptures and tears, as indicated by arrow 45, thereby breaking the hermetic seal and allowing fluid to be provided from the syringe 100 into the device 10 through the inlet port 18. For example, upon rotating either the syringe 100 or device 10, as indicated by arrow 46, the hub 104 and inlet port 18 may contact and come into threaded engagement. A person may then fill the reservoir 40 with the diluent 106 by applying pressure to a plunger 108 of the filler syringe 100, as indicated by arrow 48. As shown in FIG. 9, upon mixing of the diluent 106 with the reconstitutable agent 44, a reconstituted fluid agent 110 (which includes the agent dissolved within the diluent) is provided within the reservoir member 30.

Due to the one-way valve 26, the diluent 106 is only permitted to flow in a direction towards the reservoir 30 and prevented from flowing in a retrograde fashion out of the reservoir 30. Furthermore, the interior volume of the reservoir 30 may be within a range considered to be a micro dose, such as 0.05 ml to 1.0 ml. Accordingly, in some embodiments, the delivery device 10 does not require exact measurements when filling the reservoir 30. Instead, a person need only completely fill the reservoir with diluent 106, which includes the correct dosage, and, once completely filled, the correct dosage has been reached and the buildup of pressure will prevent the plunger 108 of the syringe 100 from advancing further. Accordingly, the device 10 allows consistent filling and dosing of the diluent 106 from device to device (e.g., filling up tens of hundreds of devices 10 at any one time). Accordingly, when in the field or directly on-site, a person may use a single filling syringe 100 to fill a plurality of delivery devices 10 in a consistent manner. The filling syringe 100 essentially acts as a means of storing and dispensing aliquots of the diluent 106.

Figure 10:
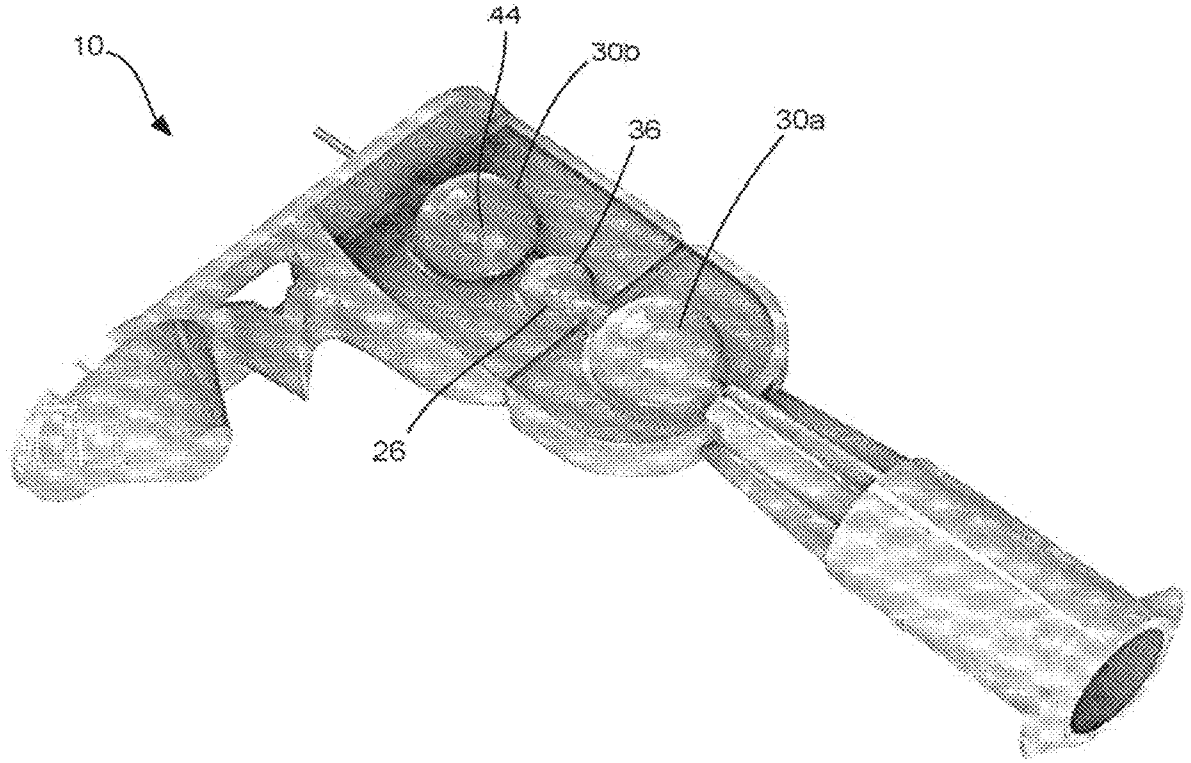
FIG. 10 is a top perspective view of another embodiment of a single use delivery device consistent with the present disclosure illustrating two separate reservoir members, one reservoir for storing a reconstitutable agent within and the other reservoir for storing a diluent within.
Figure 11:
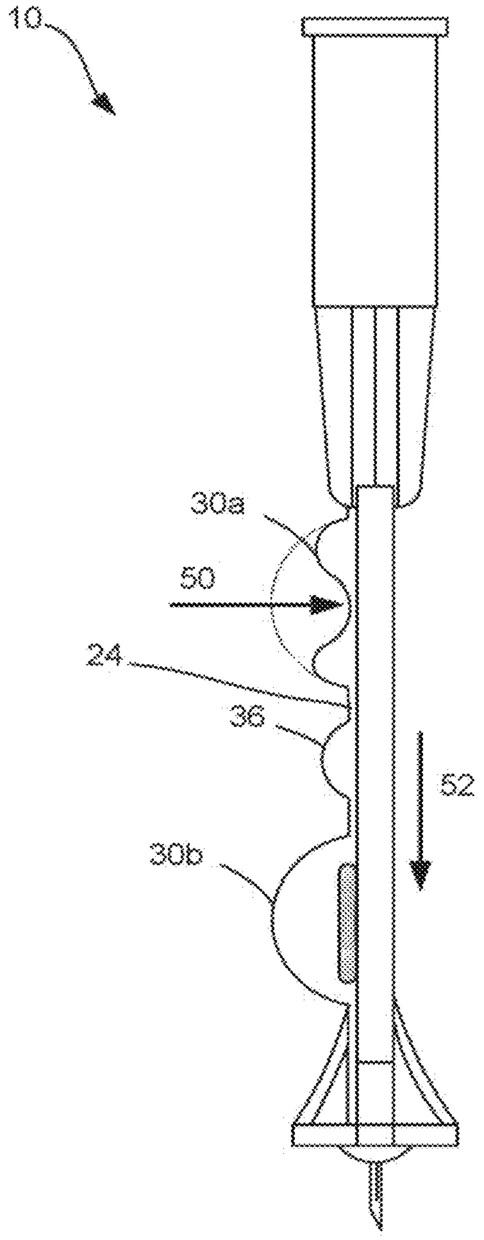
FIG. 11 is a side view of the single use delivery device of FIG. 10 illustrating dispensing of a diluent stored in the first reservoir into the second the second reservoir storing the reconstitutable agent upon compression applied thereto so as to form a reconstituted fluid agent in the second reservoir.

In some embodiments, the device 10 may be prefilled with both the reconstitutable agent 44 and diluent 106 in separate reservoirs, such that the device 10 is a standalone unit that does not require a person to couple the device 10 to a separate source of diluent for the reconstitution of the agent. For example, as shown in FIG. 10, a device 10 consistent with the present disclosure may include a top member 14 having two separate reservoirs, a first reservoir member **30*a* configured to store a dose of diluent and a second reservoir member 30*b* configured to store a dose of lyophilized agent within. The first and second reservoir members 30*a*, 30*b* are separated from one another by way of the one way valve 36. As shown, the first compressible reservoir member 30*a* is in fluid communication with the fluid pathway of the channel 24 and the second compressible reservoir member 30*b* is also in fluid communication with the fluid pathway of the channel 24. Although not shown, the first reservoir member 30*a* may generally include a temporary seal on one end adjacent to the one way valve 26 and a permanent seal on the other end adjacent to the inlet port 18. Accordingly, as shown in FIG. 11, upon sufficient compression force applied to the reservoir member 30*a*, as indicated by arrow 50, the temporary seal on the end of the reservoir member 30*a* adjacent to the one-way valve 26 may rupture or break, thereby allowing diluent stored within the first reservoir member 30*a* to be expelled therefrom and towards the second reservoir member 30*b*, as indicated by arrow 52. The diluent may then pass through the one-way valve 26 and into the interior volume of the second reservoir member 30*b* such that the diluent may mix with the reconstitutable agent 44 stored within the second reservoir member 30*b*** and form a reconstituted fluid agent ready for delivery to a patient. This particular embodiment may be advantageous in instances where a single source of diluent is either unavailable or inefficient from a cost or storage standpoint (e.g., military application).

The delivery device 10 is further configured to allow delivery of the reconstituted fluid agent to the patient in a relatively simple manner. In particular, the delivery device 10 is designed such that a person administering the reconstituted fluid agent need only position the device 10 upon the administration site (e.g., shoulder, arm, chest, nose, ear, eye, etc.), and then fully compress the reservoir 30 (or second reservoir member **30*b* of FIG. 10**) containing the dose of reconstituted fluid agent, thereby delivering the correct predefined dosage to the patient.

Figure 12A:
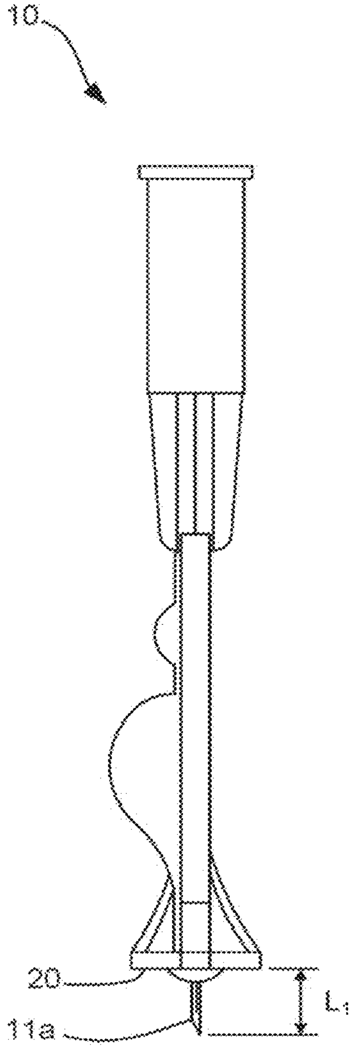
FIGS. 12A, 12B, and 12C are side views of the single use delivery device of FIG. 1 illustrating different embodiments of needles to be used for intradermal, subcutaneous, and intramuscular delivery of a reconstituted fluid agent, respectively.
Figure 12B:
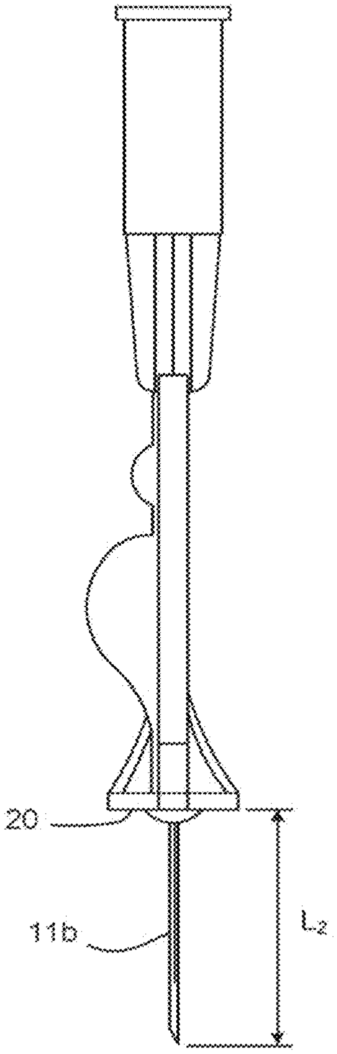
Figure 12C:
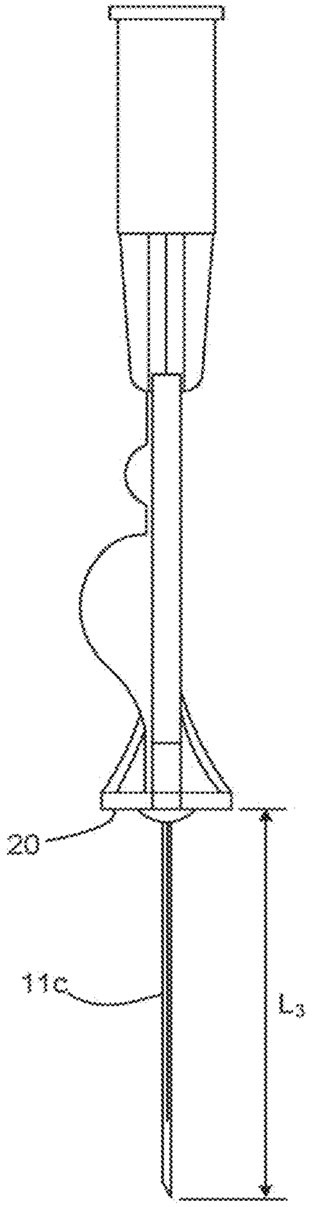
Figure 13:
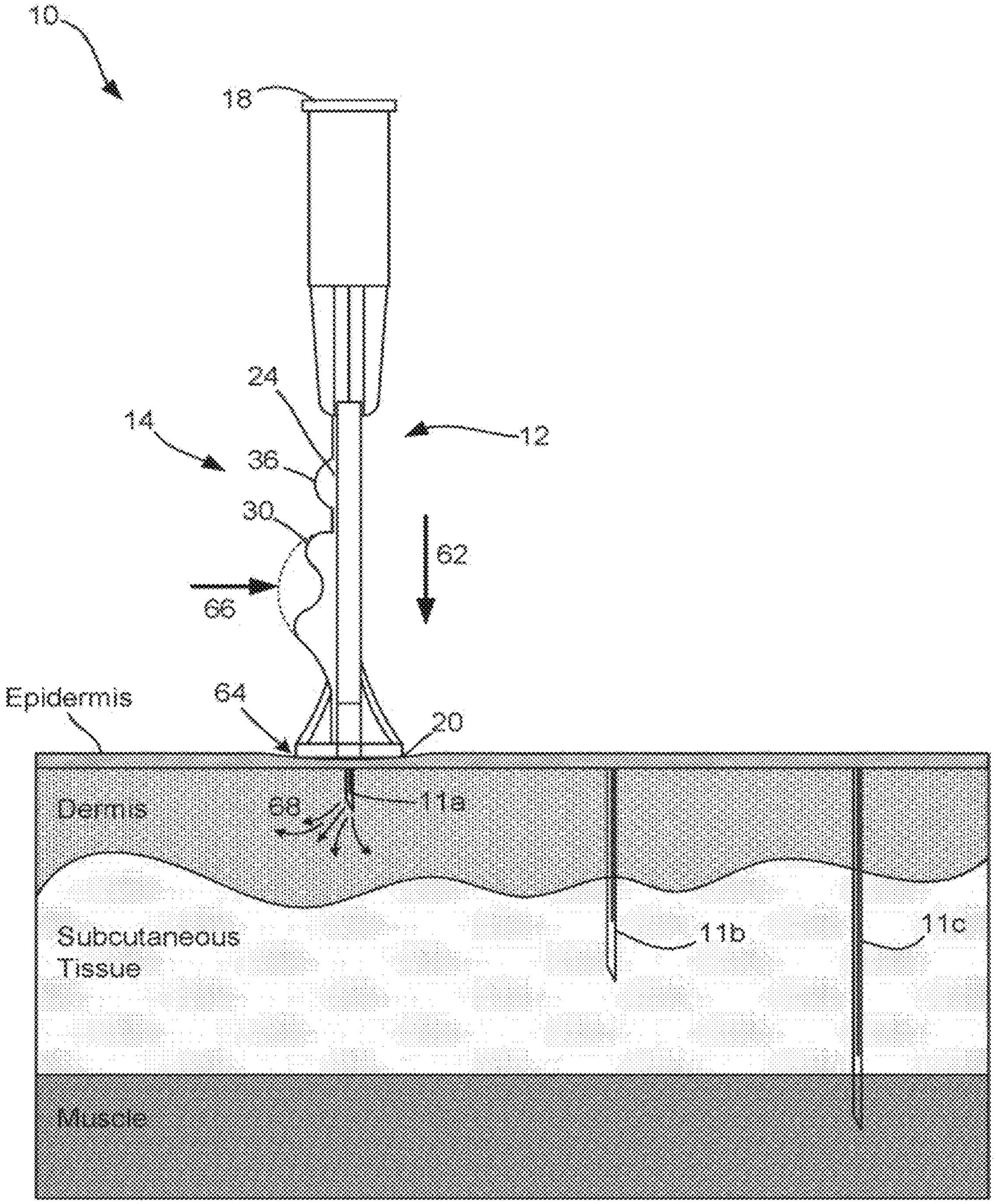
FIG. 13 illustrates intradermal, subcutaneous, and intradermal delivery of the reconstituted fluid agent with the single use delivery device of FIG. 4.

For example, once filled, the delivery device 10 is designed such that a person administering the reconstituted fluid agent 110 may easily administer a dose of the reconstituted fluid agent 110 as intended. For example, FIGS. 12A-12C are side views of the single use delivery device 10 illustrating different embodiments of needles to be used for intradermal, subcutaneous, and intramuscular delivery of a fluid agent, respectively. FIG. 13 illustrates intradermal, subcutaneous, and intradermal delivery of a fluid agent with the single use delivery device 10.

The delivery device 10 is configured to allow delivery of the reconstituted fluid agent to the patient in a relatively simple manner, without requiring specialized training for injecting a needle portion intradermally. In particular, the delivery device is designed such that a person administering the reconstituted fluid agent (e.g., administrator) need only press the delivery device against the administration site (e.g., shoulder, arm, chest, etc.), in which the device is configured such that needle penetration is limited to the correct length and orientation within the administration site. As shown, the delivery device 10 may be removed from the filler syringe 100 (or may not require the separate source of diluent, as shown in FIG. 10) and used to administer the reconstituted fluid agent as a standalone device. However, it should be noted that the delivery device 10 may remain coupled to the filler syringe 100 during administration of the fluid agent, such that an administrator may use the filler syringe 100 as a handle or means of stabilizing the delivery device 10 during delivery of the reconstituted fluid agent to a patient.

As shown in FIG. 12A, the needle **11*a* is positioned substantially perpendicular relative to a plane along which the distal end 20 of the base member 12 lies, such that the needle 11*a* is configured to be inserted into a patient's skin at a substantially perpendicular angle. This is a much more straightforward process for intradermal delivery of an agent, particularly when compared to the Mantoux procedure. Furthermore, the distal end is configured to contact the patient's skin during penetration of the needle 11*a*, thereby indicating adequate depth of penetrating for intradermal injection of the reconstituted fluid agent. For example, the needle 11a may be a micro-needle having a length $L_1$ (measured from the distal end 20**) in the range of 0.5 mm to 4 mm.

Other needles may be used with devices 10 of the present disclosure. For example, as shown in FIG. 12B, the device 10 may include a needle 11b specifically designed for subcutaneous delivery of a reconstituted fluid agent. For example, the needle 11b may have a length $L_2$ (measured from the distal end 20) in the range of 8 mm to 15 mm. As shown in FIG. 12C, the device 10 may include a needle 11c specifically designed for intramuscular delivery of a reconstituted fluid agent, such that the 11c has a length $L_3$ (measured from the distal end 20) in the range of 18 mm to 30 mm.

Accordingly, as shown in FIG. 13, upon an administrator applying pressure in a direction towards the target site, as indicated by arrow 62, the needle 11a is configured to penetrate the epidermis and dermis layers of skin. Needle 11b is configured to penetrate the epidermis, dermis and subcutaneous layers. Needle 11c is configured to penetrate the epidermis, dermis, subcutaneous, and muscle layers. Upon sufficient contact between the distal end of the base member 12 and the outer layer of skin, as indicated by arrow 64, the needles 11a, 11b, 11c have achieved adequate penetration into the dermis for injection of the reconstituted fluid agent into the appropriate layer. For example, upon the needle 11a reaching the adequate depth into the dermis, the administrator may then compress the reservoir member 30 (second reservoir member 30b for embodiment of FIG. 10) containing the dosage of reconstituted fluid agent so as to deliver the fluid agent into the dermis. For example, the reservoir member 30 is configured to substantially collapse and reduce the interior volume upon substantial compression applied thereto, as indicated by arrow 66. An administrator need only fully compress the reservoir member 30 so as to expel to required dosage. Upon compression of the reservoir member 30, the reconstituted fluid agent is expelled into the fluid pathway of the channel 24 and out of the outlet port 22 and out of the needle 11, resulting in delivery of the fluid agent into the dermis, as indicated by arrow 68.

In some embodiments, the reservoir member 30 is shaped or sized such that, upon compression applied thereto, the reservoir member 30 is prevented from being reformed and the interior volume is prevented from expanding subsequent to substantial compression. Additionally, or alternatively, the valve cover 36 may be shaped or sized such that, upon compression applied thereto, the valve cover 36 is configured to substantially collapse upon the one-way valve 26 and render the one-way valve 26 inoperable, thereby blocking fluid flow into or out of the one-way valve 26. Accordingly, the delivery device 10 configured to be rendered incapable of reuse following its delivery of the reconstituted fluid agent to a patient, thereby preventing reuse of the device and reducing the risk of the spreading blood-borne diseases through reuse.

Accordingly, the delivery device 10 of the present invention does not require a trained, skilled healthcare profession for administration of vaccines or drugs. As such, the delivery device may be particularly useful in situations in which vaccines or drugs are being administered in non-healthcare related facilities (e.g., outside of clinics or hospitals) and given to large numbers of individuals over a short period of time by a non-professional.

Figure 14A:
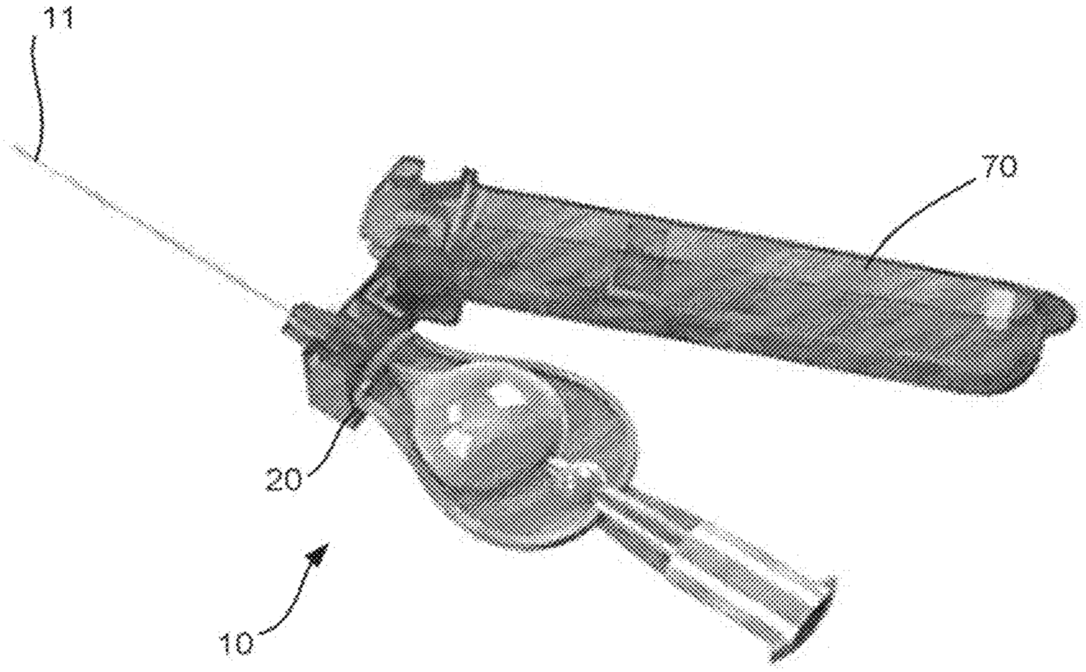
FIGS. 14A and 14B are perspective views of another embodiment of a needle protector in an open position, in which the penetrating tip of the needle is exposed, and a closed position, in which at least the penetrating tip of the needle is shielded and covered.
Figure 14B:
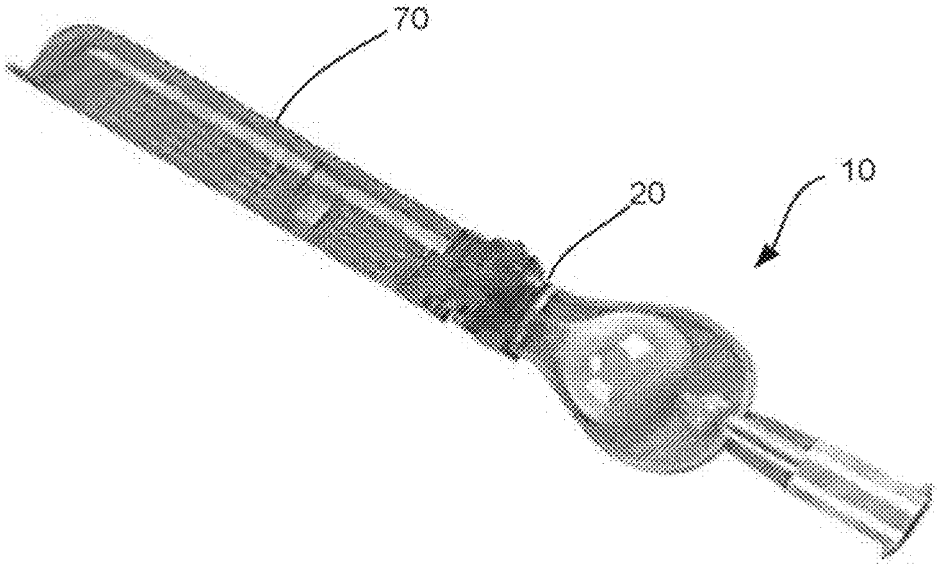

It should further be noted that, in order to compensate for the variety of different lengths of needles 12a-12c, the device 10 may further include an alternative embodiment of a needle protector. FIGS. 14A and 14B are perspective views of a needle protector member 70 in an open position, in which the penetrating tip of the needle 11 is exposed, and a closed position, in which at least the penetrating tip of the needle 11 is shielded and covered by the needle protector member 70. Similar to needle protector member 38 previously described herein, needle protector member 70 generally extends from the distal end 20 of the device 10 and is adjacent to the outlet port. The needle protector member 70 may be coupled to the distal end 20 by way of any known means. In the illustrated embodiment, the needle protector member 70 is coupled to the distal end 20 by way of a living hinge, for example. Accordingly, the needle protector member 70 is configured to move between a closed position and an open position. The needle protector member 70 is shaped and/or sized so as to accommodate needles of a specific length (e.g., needles having a length between 0.5 and 30 mm or longer). For example, when in a closed position, as shown in FIG. 14B, the needle protector member 70 is configured to substantially enclose at least the penetrating tip of a needle 11, wherein the needle may have a length between 4 mm and 30 mm or longer, such that the needle protector member 38 would be inadequate and would not accommodate a needle of such length. When in an open position, as shown in FIG. 13A, the penetrating tip of the needle 11 is exposed and ready for intradermal injection on a target site of a patient.

As generally understood, a therapeutic agent, medicament, fluid agent, drug, or the like, can be administered to a patient in a variety of different ways, or different routes of medication administration. A route of administration is the path by which therapeutic agent, medicament, fluid agent, drug is taken into the body. Common routes of administration include, but are not limited to, oral, intravenous, intradermal, intramuscular, subcutaneous, transdermal, epicutaneous or topical, nasal and transmucosal, intraocular or intravitreal (through the eye), and others.

It should be noted that the single use delivery device 10 of the present disclosure is not limited solely to the administration of a fluid agent via an injection needle (e.g., intravenous, intramuscular, intradermal, or subcutaneous route of administration). For example, in other embodiments, a delivery device 10 consistent with the present disclosure may be fitted with an administration member configured to deliver a fluid agent via a different route of administration in lieu of the use of a needle. For example, in other embodiments, the administration member may include a nozzle configured to control administration of the reconstituted fluid agent to the patient. The nozzle may include a spray nozzle, for example, configured to facilitate dispersion of the reconstituted fluid agent into a spray. Accordingly, a delivery device fitted with a spray nozzle may be particularly useful in the administration of a fluid agent into the nasal passage, for example, or other parts of the body that benefit from a spray application (e.g., ear canal, other orifices). In other embodiments, the nozzle may be configured to facilitate formation of droplets of the fluid agent. Thus, a delivery device including a droplet nozzle may be useful in the administration of a fluid agent by way of droplets, such as administration to the eyes, topical administration, and the like.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A single use delivery device comprising:

an administration member for administering a fluid agent to a patient; and a delivery assembly coupled to said administration member and configured to provide said fluid agent to said administration member, said delivery assembly comprising:

an outlet port coupled to said administration member;

a first compressible reservoir member comprising the fluid agent stored within a first interior volume thereof;

a second reservoir member;

a channel providing a fluid pathway from said first compressible reservoir member to said second reservoir member and from said second compressible reservoir member to said outlet port;

a seal closing the fluid pathway between the first compressible reservoir and the second reservoir member; and wherein said delivery assembly is configured such that a compression of said first compressible reservoir expels said fluid agent through said seal and into said second reservoir member and wherein said second reservoir member is configured to receive said fluid agent passing through said seal and expel said fluid agent into said fluid pathway and through said outlet port into said administration member.

2. The single use delivery device of claim 1, wherein said delivery assembly further comprises a protector member adjacent to said outlet port and configured to move between a closed position, in which at least a tip of said administrator member is shielded, and an open position, in which said tip of said administration member is exposed.

3. The single use delivery device of claim 2, wherein said protector member is coupled to said delivery assembly via a living hinge.

4. The single use delivery device of claim 1, wherein said administration member comprises a needle for at least one of subcutaneous, intramuscular, intradermal, and intravenous injection of said combined agent into said patient.

5. The single use delivery device of claim 4, wherein said needle has a length in the range of 0.5 mm to 30 mm.

6. The single use delivery device of claim 1, wherein said administration member comprises a nozzle configured to control administration of said fluid agent to said patient.

7. The single use delivery device of claim 1, wherein said delivery assembly, further comprises:

a feature of said fluid pathway of said channel disposed between said first and second reservoir members, said feature configured to limit flow of said fluid agent to an antegrade direction from said first compressible reservoir member toward said outlet port.

8. The single use delivery device of claim 1, wherein said first interior volume of said first compressible reservoir member is in the range of 0.05 ml to 1.0 ml.

9. A single use delivery device for delivering a fluid agent to a patient, said single use delivery device comprising:

a proximal end and a distal end, said distal end having an outlet port configured to provide a fluid agent for delivery to a patient;

a channel providing a fluid pathway extending a length from said proximal end to said outlet port;

a first compressible reservoir member comprising said fluid agent stored within a first interior volume thereof, said first compressible reservoir member being in communication with said fluid pathway and being disposed adjacent to said proximal end;

a second reservoir member in communication with said fluid pathway and being disposed adjacent to said distal end;

a feature of said fluid pathway of said channel disposed between said first and second reservoir members, said feature comprising a seal closing the fluid pathway between the first compressible reservoir and the second reservoir member; and wherein upon a compression of said first compressible reservoir, said fluid agent is expelled through said feature and into said second reservoir member; and wherein said second reservoir member is configured to expel said fluid agent into said fluid pathway and through said outlet port in response to a compression force applied to the delivery device.

10. The single use delivery device of claim 9, further comprising an administration member coupled to said outlet port and configured to administer said combined agent to said patient, and wherein said feature comprises a first feature, further comprising, a second feature configured to limit flow to an antegrade direction from said proximal end toward said outlet port.

11. The single use delivery device of claim 10, wherein said administration member comprises a needle for at least one of subcutaneous, intramuscular, intradermal, and intravenous injection of said combined agent into said patient.

12. The single use delivery device of claim 10, wherein said administration member comprises a nozzle configured to control administration of said combined agent to said patient, wherein said nozzle is configured to facilitate dispersion of said combined agent into spray or one or more droplets.

13. A single use delivery device comprising:

an administration member for administering a combined agent to a patient; and a delivery assembly coupled to said administration member and configured to provide said combined agent to said administration member, said assembly comprising:

an outlet port coupled to said administration member;

a first compressible reservoir member comprising a first agent stored within a first interior volume thereof, a second reservoir member comprising a second agent stored within a second interior volume thereof;

a channel providing a fluid pathway from said first compressible reservoir member to said second reservoir member and from said second reservoir member to said outlet port;

a seal closing the fluid pathway between the first compressible reservoir and the second reservoir member; and wherein said delivery device is configured upon a compression of said first compressible reservoir, to expel said first agent through said seal and into said second reservoir member and wherein said second reservoir member comprising said second agent stored within said second interior volume thereof is configured to receive said first agent passing through said seal valve to enable mixing of said first agent with said second agent to thereby create the combined agent, and to expel said combined agent into said fluid pathway and through said outlet port into said administration member in response to a compression force applied to the delivery device.

14. The single use delivery device of claim 13, wherein said second agent is selected from the group consisting of a lyophilized agent, a powdered agent, a granular agent, an agent embedded in a reconstitutable material, and combinations thereof.

15. The single use delivery device of claim 13, wherein said delivery assembly further comprises a protector member adjacent to said outlet port and configured to move between a closed position, in which at least a tip of said administrator member is shielded, and an open position, in which said tip of said administration member is exposed.

16. The single use delivery device of claim 13, wherein said administration member comprises a needle for at least one of subcutaneous, intramuscular, intradermal, and intravenous injection of said combined agent into said patient.

17. The single use delivery device of claim 16, wherein said needle has a length in the range of 0.5 mm to 30 mm.

18. The single use delivery device of claim 13, wherein said administration member comprises a nozzle configured to control administration of said combined agent to said patient.

19. The single use delivery device of claim 13, wherein said delivery assembly, further comprises:

a one-way valve positioned within said fluid pathway of said channel and disposed between said first and second reservoir members, said one-way valve configured to limit flow of said first agent to an antegrade direction from said first compressible reservoir member toward said outlet port.

20. The single use delivery device of claim 13, wherein said first interior volume of said first compressible reservoir member is in the range of 0.05 ml to 1.0 ml.

* * * * *